United States Patent [19]

Nakamura et al.

[11] Patent Number: 5,187,572
[45] Date of Patent: Feb. 16, 1993

[54] ENDOSCOPE SYSTEM WITH A PLURALITY OF SYNCHRONIZED LIGHT SOURCE APPARATUSES

[75] Inventors: Kazunari Nakamura; Kei Takasugi, both of Hachioji, Japan

[73] Assignee: Olympus Optical Co., Ltd., Tokyo, Japan

[21] Appl. No.: 785,402

[22] Filed: Oct. 30, 1991

[30] Foreign Application Priority Data

Oct. 31, 1990 [JP] Japan .................................. 2-296831
Aug. 27, 1991 [JP] Japan .................................. 3-215542

[51] Int. Cl.⁵ ............................ A61B 1/04; A61B 1/06
[52] U.S. Cl. ............................................ 358/98; 128/6
[58] Field of Search ............................... 358/98; 128/6

[56] References Cited

U.S. PATENT DOCUMENTS 5,078,150 1/1992 Hara ........................................ 358/98

Primary Examiner—Howard W. Britton
Attorney, Agent, or Firm—Armstrong, Westerman, Hattori, McLeland, Naughton

[57] ABSTRACT

An electronic endoscope is provided with a photoelectrically converting solid state imaging device and a light guide transmitting an illuminating light. A video signal processing circuit processes signals for the solid state imaging device. The electronic endoscope, the light guide and the video signal processing circuit are selectively connected and have a first light source and second light source for supplying different illuminating lights, respectively. Where the two light sources receive synchronizing signals from the video signal processing circuit and synchronized each other, the two light sources can supply the illuminating lights to a light guide. When the connection of the light guide is changed, the disorder of a picture image can be reduced.

24 Claims, 23 Drawing Sheets

FIG.15
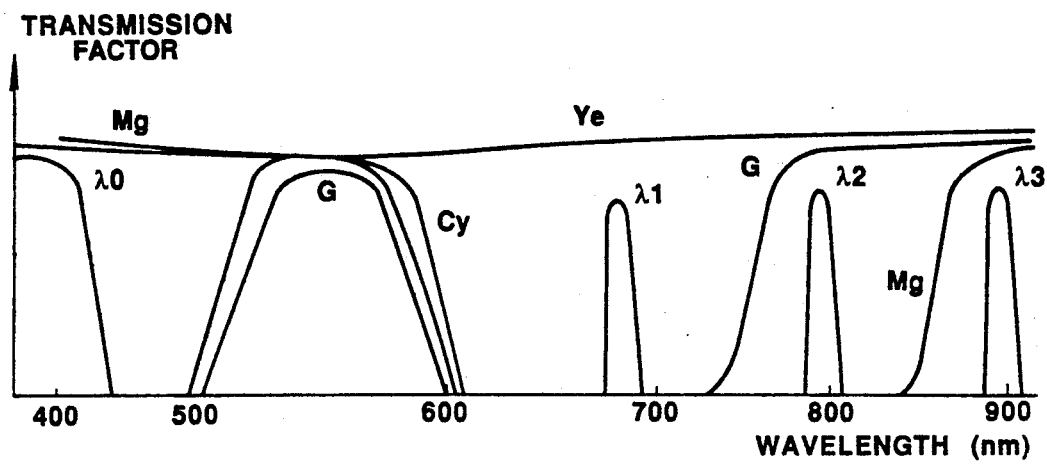
FIG.16a        FIG.16b
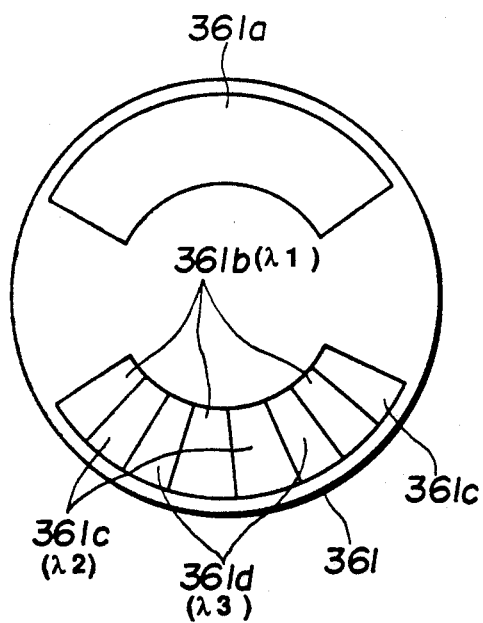    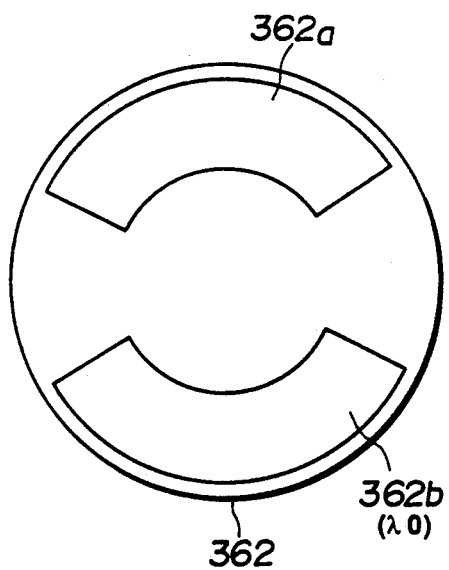

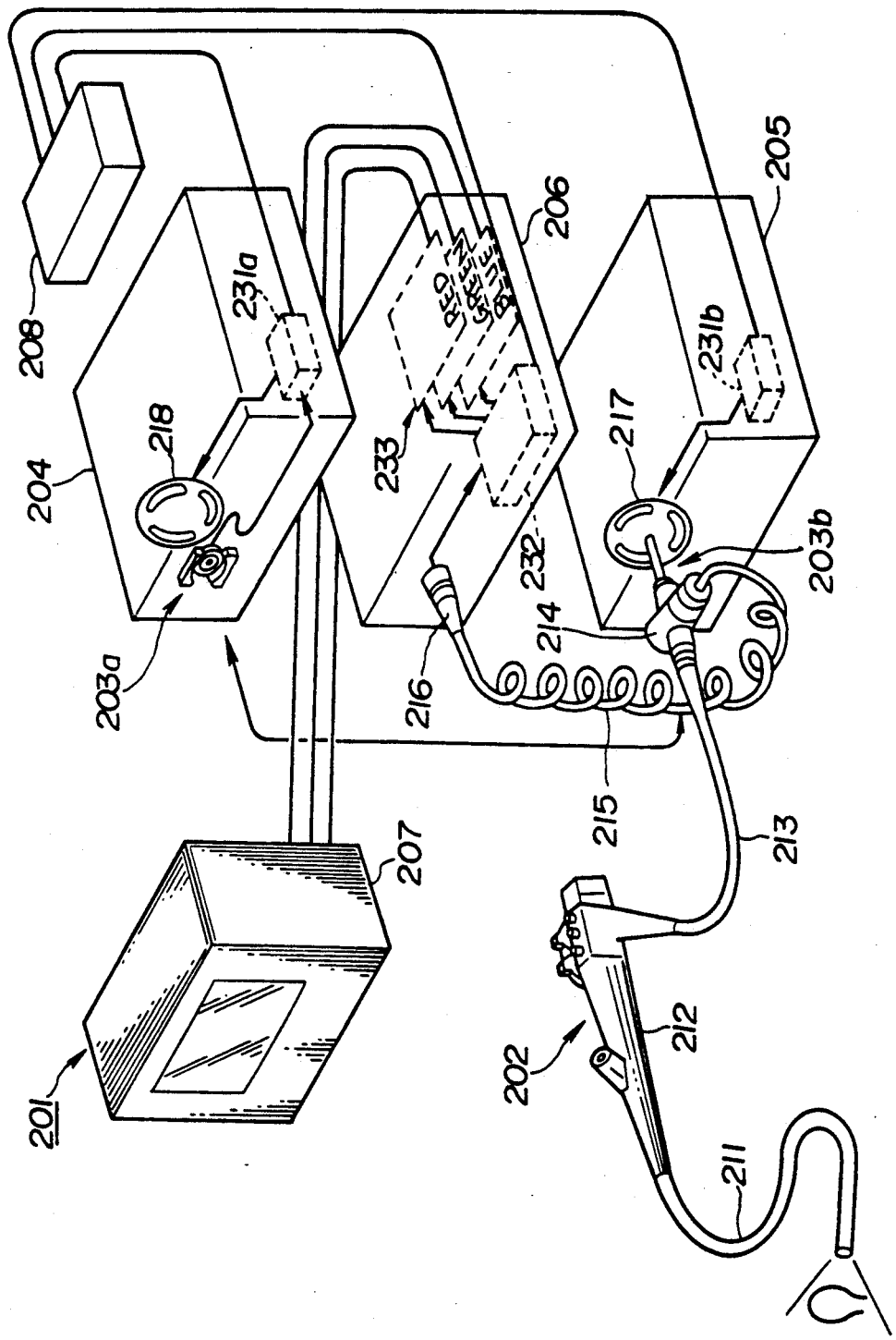

ENDOSCOPE SYSTEM WITH A PLURALITY OF SYNCHRONIZED LIGHT SOURCE APPARATUSES

BACKGROUND OF THE INVENTION

FIELD OF THE INVENTION AND RELATED ART STATEMENT

The present invention generally relates to an endoscope system in which a plurality of light source apparatuses, which can be used by switching, are synchronized with a common video signal processing apparatus by a synchronizing signal to obtain a plurality of different picture images.

Recently, an endoscope has been widely used whereby, by inserting an elongated insertable part of the endoscope into the body cavity, internal organs in the body cavity can be observed and several kinds of medical treatments can be applied by using the treatment tools inserted into treatment channels as the occasion demands. Also, various electronic endoscopes in which a solid state imaging device, such as a CCD, is used in an imaging system have been proposed.

It has been recognized that knowing the distribution of the quantity of hemoglobin and the distribution of the degree of saturation with oxygen in blood is helpful in early discovery of a pathological change. It has also been recognized that the observation of the images not only in a visible light range but also in an infrared rays range allows to observe a pathological change which is difficult to be observed in an ordinary visible light range.

For example, as shown in the Gazette of Japanese Patent Laid Open No. 217415/1989, an apparatus having a plurality of filers (including at least a filter which can sequentially separate a light emitted from a light source into three wavelength ranges where a color picture can be formed) are insertably arranged in the light source and on the illuminating optical path and filter switching means where one of the above mentioned plurality of filters can be selectively inserted on the illuminating optical path is disclosed so that a plurality of lights including a frame sequential light which can form a color picture image can be supplied by switching the filters with the filter switching means.

Also, as shown in the Gazette of Japanese Patent Laid Open No. 76827/1989, in an electronic endoscope apparatus displaying a video signal of a subject image, such as an affected part taken by an imaging device of CCD or the like on a monitor TV fitted outside, a device which is operated is disclosed as having first irradiating means for irradiating a subject with near infrared rays, second irradiating means for irradiating a subject with visible rays through a light guide and selecting control means for selecting either case of the first or second irradiating means.

However, the structure of the above mentioned Japanese Patent Laid Open No. 217415/1989 has a problem. That is, since a driving part for selecting a plurality of rotary filters is provided and is used for a special examination which is not needed for an ordinary observation, the light source body becomes larger, at the same time, an effective exclusive light source cannot be used.

Also, the device shown in Japanese Patent Laid Open No. 76827/1989 has a problem whereby the device cannot be used for a system requiring a shading period of an illuminating light and cannot process a characteristic requiring attention by making the characteristic remarkable by a picture image calculation among different wavelengths because only one wavelength, such as a laser beam, is used.

OBJECT AND SUMMARY OF THE INVENTION

An object of the present invention is to provide an endoscope system which can supply various illuminating lights so as to obtain various picture images of different observing wavelength ranges depending on an observing part or purpose.

Another object of the present invention is to provide an endoscope system by which a picture image is in little disorder at switching light sources even if using light source apparatus is switched.

The present invention is provided with an electronic endoscope having first illuminating means for emitting illuminating lights of various wavelength range in a time series, second illuminating means for emitting illuminating lights of different wavelength ranges from the illuminating lights of the first illuminating means for and imaging means imaging a subject under the first and second illuminating means, respectively, video signal processing means for reading a picture signal photoelectrically converted by the imaging means and producing a standard video signal, and synchronizing control means for synchronizing the illuminating light emitted by the first illuminating means with the illuminating light emitted by the second illuminating means by using a synchronizing signal synchronized with a read timing of the picture signal by the video signal processing means. Thus, the illuminating means can be switched depending on an observing part or purposes and different picture information can be obtained depending on each illuminating light. Also, the disorder in picture images when the images are switched can be reduced by the synchronizing control of the synchronizing control means.

BRIEF DESCRIPTION OF THE DRAWINGS

FIG. 1 is a formation diagram showing an endoscope apparatus of the first embodiment of the present invention.

FIG. 2 is a front view showing a rotary disk.

FIG. 3 is a front view showing a rotary filter contained in a second light source.

FIG. 4 is a block diagram showing a formation of a CCU or the like.

FIG. 5 is an explanatory view of the operation of the first embodiment.

FIG. 6 is a formation diagram showing an endoscope apparatus of the second embodiment of the present invention.

FIG. 7 is a front view showing a rotary filter contained in a first light source.

FIG. 8 is a characteristic diagram showing transmission factor characteristics of filters fitted to a rotary filter.

FIG. 9 is a block diagram showing main parts of a CCU.

FIG. 15 is a characteristic diagram showing transmission factor characteristics of the color separating filters or the like used in an endoscope apparatus in FIG. 11.

FIG. 16 is an explanatory view of a rotary filter used in first and second light sources.

FIG. 33 is a formation diagram showing an endoscope apparatus where operability for switching an ordinary observation and a blood flow observation is improved.

DETAILED DESCRIPTION OF THE PREFERRED EMBODIMENTS

Figure 1:
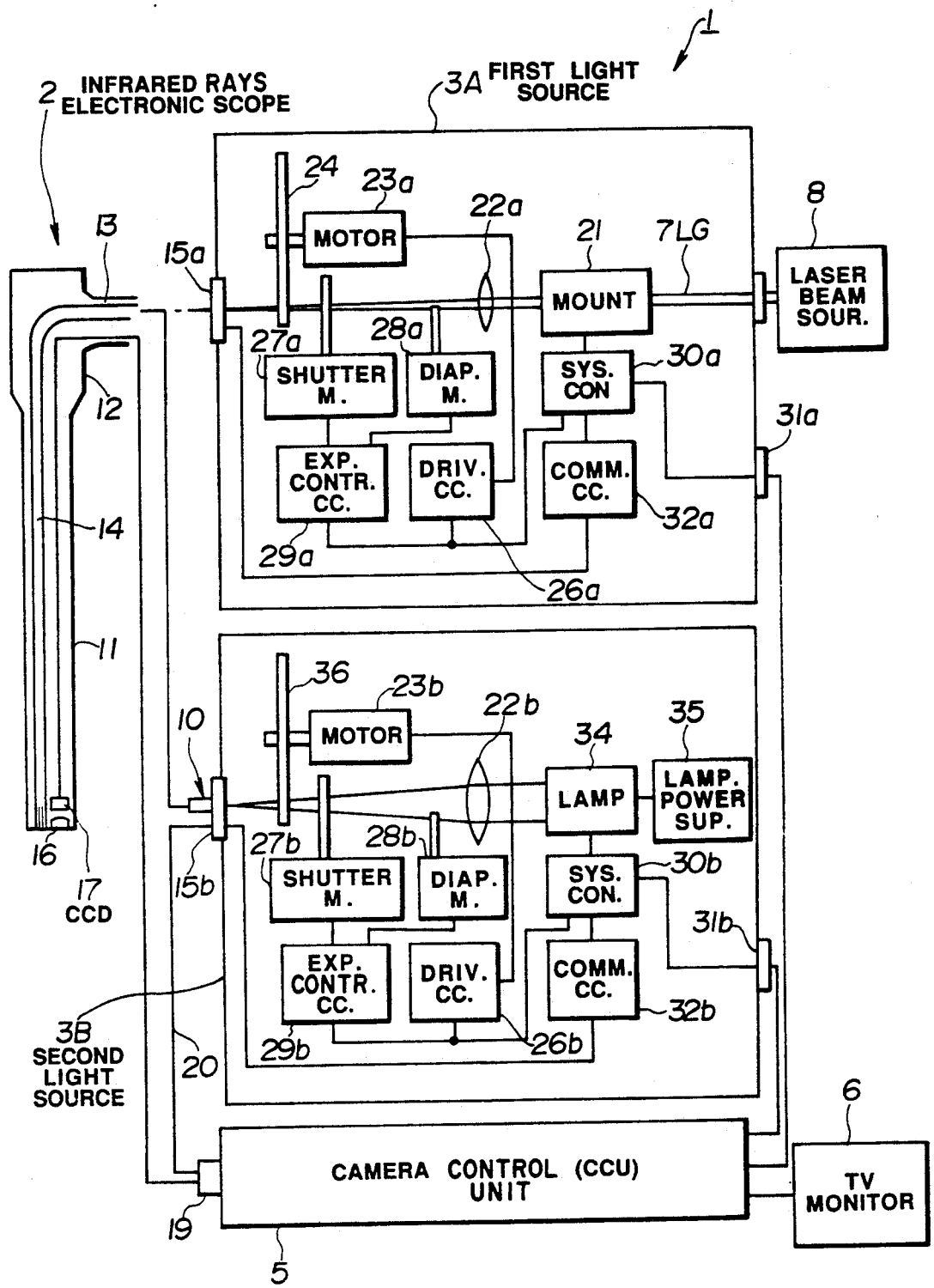
FIGS. 1 to 5 relate to the first embodiment of the present invention.

Embodiments of the present invention will be explained by referring to the drawings as follows.

As shown in FIG. 1, an endoscope apparatus 1 of the first embodiment contains imaging means and includes an infrared rays electronic scope 2 being sensitive to infrared rays, a first light source 3A supplying a first illuminating light to the infrared rays electronic scope 2, a second light source 3B supplying a second illuminating light to the infrared rays electronic scope 2, a camera control unit (hereinafter, referred to as CCU) 5 processing a video signal for the infrared rays electronic scope 2, a TV monitor 6 displaying the video signal processed by the CCU 5 and a laser beam source 8, connected to the first light source 3A through a light guide 7, for emitting infrared rays.

The above mentioned infrared rays electronic scope 2 contains an elongated insertable part 11, a broad operating part 12 formed at the rear end of the insertable part 11 and universal cable 13 extending from the operating part 12. A light guide 14 for transferring an illuminating light is inserted into the insertable part 11 and also inserted into the universal cable 13. A light source connector 10, which is the end of the light guide 14, can be connected to an output connector receiver 15a or 15b of the first light source 3A or the second light source 3B.

An objective lens 16 is fitted to the distal end of the insertable part 11. A CCD 17 is arranged at the focal surface of the objective lens 16. An infrared cut filter is removed from the CCD 17 and the CCD 17 uses a filter having a characteristic of the sensitivity in the infrared rays range. In the signal line of the CCD 17, a signal connector 19 which branches off from the light connector 10 can be connected to the connector receiver of the CCD 5. The output signal of the CCD 17 is processed by the CCD 5.

The first light source 3A emits light from the output connector receiver 15a on the illuminating optical path to the light guide 14 of the electronic scope 2 by using a lens 22a which converges infrared rays from the light guide 7 fitted to a mount 21. On the illuminating optical path, a rotary disk 24a rotated by a motor 23a is arranged to make a time series intermittent light of an illuminating light by the rotary disk 24a.

Figure 2:
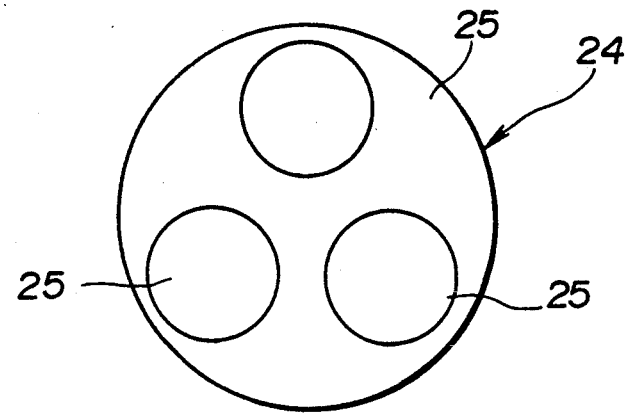

That is, in the rotary disk 24a, three transmitting parts, each referred to by reference number, are provided in the circumference direction as shown in FIG. 2. The above mentioned motor 23a is driven by a driving circuit 26a.

Also, shutter means 27a is insertably provided on the above mentioned illuminating optical path. The shutter means 27a has a function of cutting an illuminating light when the light source connector 10 is drawn from the output connector receiver 15a.

Based on an exposure control signal from the CCU 5, diaphragm means 28a for adjusting the quantity of illuminating light is provided and driven by an exposure controlling circuit 29a.

The driving circuit 26a and exposure controlling circuit 29a are controlled by a system controller 30a. A vertical synchronizing signal VD is fed into the system controller 30a through a light source connector 31a from the CCU 5. The system controller 30a has a communication circuit 32a communicating through CCU 5 and the infrared rays electronic scope 2. The communication circuit 32a can communicate with the CCU 5 through a communication line 20 provided between the light source connector 10 and the signal connector 19 by the connection of the light source connector 10 of the infrared rays electronic scope 2 connected to the output connector 15a.

Figure 3:
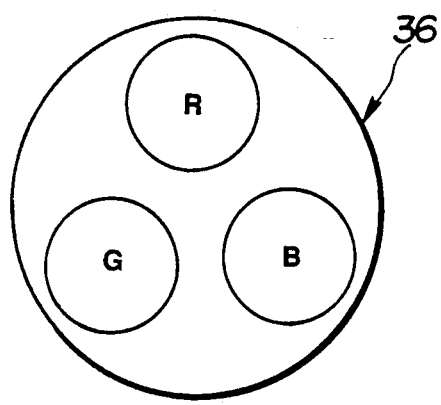

Meanwhile, a lamp 34 emitting light in a visible light range is fitted in the second light source 3B instead of the mount 21 of the first light source 3A and emits light with the electric power supplied from a lamp power supply 35. Also, a rotary filter 36 provided with filters R, G and B is used in the second light source 3B instead of the rotary disk 24 in the first light source 3A. As shown in FIG. 3, the filters R, G and B (abbreviated as R, G and B in FIG. 3) for transmitting the wavelength ranges of R, G and B, respectively, are fitted into the rotary filter 36.

The other structure is the same as the first light source 3B. The same structure elements are given the same reference numerals and mark b instead of mark a.

Figure 4:
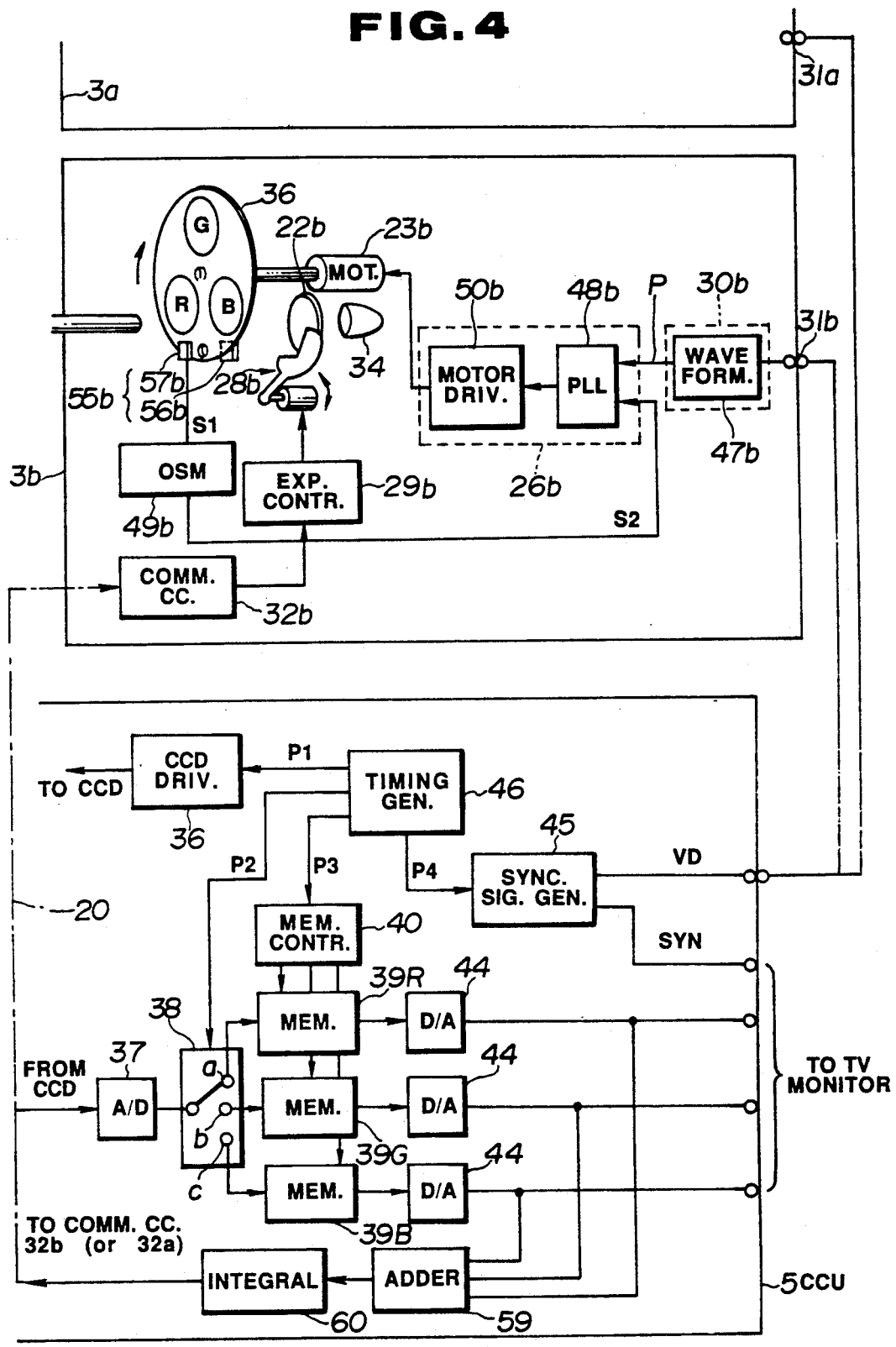

FIG. 4 shows a concrete example wherein the structure of CCU 5 and, for example, the second light source are kept as the synchronized condition with a synchronizing signal.

The CCU 5 contains a CCD driving circuit 36 for supplying a CCD driving signal for driving the CCD 17. The CCD driving signal is applied to the CCD 17. By this application, the picture signal photoelectrically converted at the CCD 17 is read from the CCD 17, fed into an A/D converter 37 and converted into a digital signal. The signal is written in three frame memories 39R, 39G and 39B through a switching switch 38 one by one under the control of a memory controller 40. Further, each of the frame memories 39R, 39G and 39B actually includes two frame memories. The frame memory to be written and the frame memory to be read are alternately switched.

The picture signal data written in the frame memories 39R, 39G and 39B are synchronized with a synchronizing signal SYN and simultaneously read, and then converted into three analog primary color signals at a D/A converter 44, respectively. The picture signal is supplied to the TV monitor 6 with a synchronizing signal SYN consisting of horizontal and vertical synchronizing signals, and picture images imaged by synchronizing with the synchronizing signal SYN are displayed on the monitor 6. Since the second light source 3B emits the illuminating lights R, G and B, the displayed picture images become color picture images observed under a white illuminating light, while the picture image under the illumination of the infrared rays is displayed in almost monochrome (black and white) because the first light source 3A emits infrared rays (instead of the illuminating lights R, G and B in the case of the second light source 3B, respectively); and A timing signal is supplied from a timing generator 46 to the CCD driving circuit 36, the switching switch 38, the memory controller 40, and a synchronizing signal generating circuit 45 where the synchronizing signal SYN is produced. For example, a pulse P1 dividing one frame period (for example, 1/30 second) into three equal parts is applied to the CCD driving circuit 36 as a timing signal, as shown in FIG. 5a, and the CCD driving circuit 36 is synchronized with the pulse P1 so that a vertical transmitting pulse $\phi V$ and horizontal transmitting pulse $\phi H$, shown in FIGS. 5e and 5f, are fed to the CCD 17 as a CCD driving signal.

A switching pulse P2, shown in FIGS. 5b, 5c and 5d, is applied to the switching switch 38. By the switching pulse P2, contact points a, b and c are made to be ON one by one. The pulse P3 synchronized with the above mentioned pulse P1 is applied to the memory controller 40 so that the memory controller 40 supplies an address signal for writing to the frame memories 39R, 39G and 39B one by one. Thus, the picture signal data supplied through a contact point i (i=a, b or c) which in ON is written in a frame memory 39I (I=A, G or B). Also, the data is synchronized with a pulse P4 which is supplied once by one frame from a timing generator 46 in a synchronizing signal generating circuit 45, as shown in FIG. 5j, and a vertical synchronizing signal VD constituent (which is displayed as interlace) shown in FIG. 5k (in the synchronizing signal SYN) is supplied to the first and second light sources 3A and 3B.

The vertical synchronizing signal VD is fed to the system controllers 30a and 30b through the light source connectors 31a and 31b. As shown in FIG. 4, a rectangular pulse (duty is 50%) P having a cycle of one frame period, as shown in FIG. 5l, is produced by a waveform shaping circuit 47b of the system controller 30b (in the same way as 30a) shown in FIG. 4. The rectangular pulse P is supplied to a PLL circuit 48b forming the driving circuit 26b with the output of an one-shot multivibrator (abbreviated as OSM) 49b. The output of the PLL circuit 48b is inputted into the motor 23b through a motor driving circuit 50b.

A position detecting signal S1 (see FIG. 5h) of a sensor 55b for detecting the rotary position of the rotary filter 36 is fed into the above mentioned OSM 49b. In order to provide a trigger signal of the position detecting signal S1, the OSM 49b supplies a signal S2 shown in FIG. 5i to the PLL circuit 48b. The above mentioned sensor 55b includes, for example, a photo-interrupter. A pair of luminous device 56b and acceptance device 57b are arranged so as to place a part of the circumference of the rotary filter 36 between these devices. When a hole 58b reaches a part of the circumference of the rotary filter 36 coincides with the position where these luminous device 56b and acceptance device 57b face each other, the acceptance device 57b generates a signal S1 shown in FIG. 5h. In this embodiment, the position of the hole 58b is adjusted so that the signal S1 can be supplied by the timing of, for example, the red filter R's withdrawal from the optical path, that is, the end of the illuminating period of red light. If the timing of the beginning of the illuminating period is detected, the same operation is carried out provided that the read timing for the CCD 17 is shifted so as to make a shading period.

The above mentioned PLL circuit 48b controls the rotation of the motor 23b to make the phases of two signals P and S2 coincide (see the coincidence of FIGS. 5l and 5i). In other words, even if the phases of the signals P and S2 do not coincide, these phases are controlled to be coincided by a PLL function and the coincided condition is fixed thereafter. In this condition, the illuminating light supplied to the light guide 14 through the rotary filter 36 has a timing which terminates a red illuminating period when the signal S2 becomes "H", as shown in FIG. 5g and also, as shown in FIGS. 5e and 5f, CCD driving signals are generated by this timing. Also, in this period, a contact point is ON in the pulse P2, shown in FIG. 5b, and the signal supplied from the CCD 17 is stored in the frame memory 39R.

Figure 5:
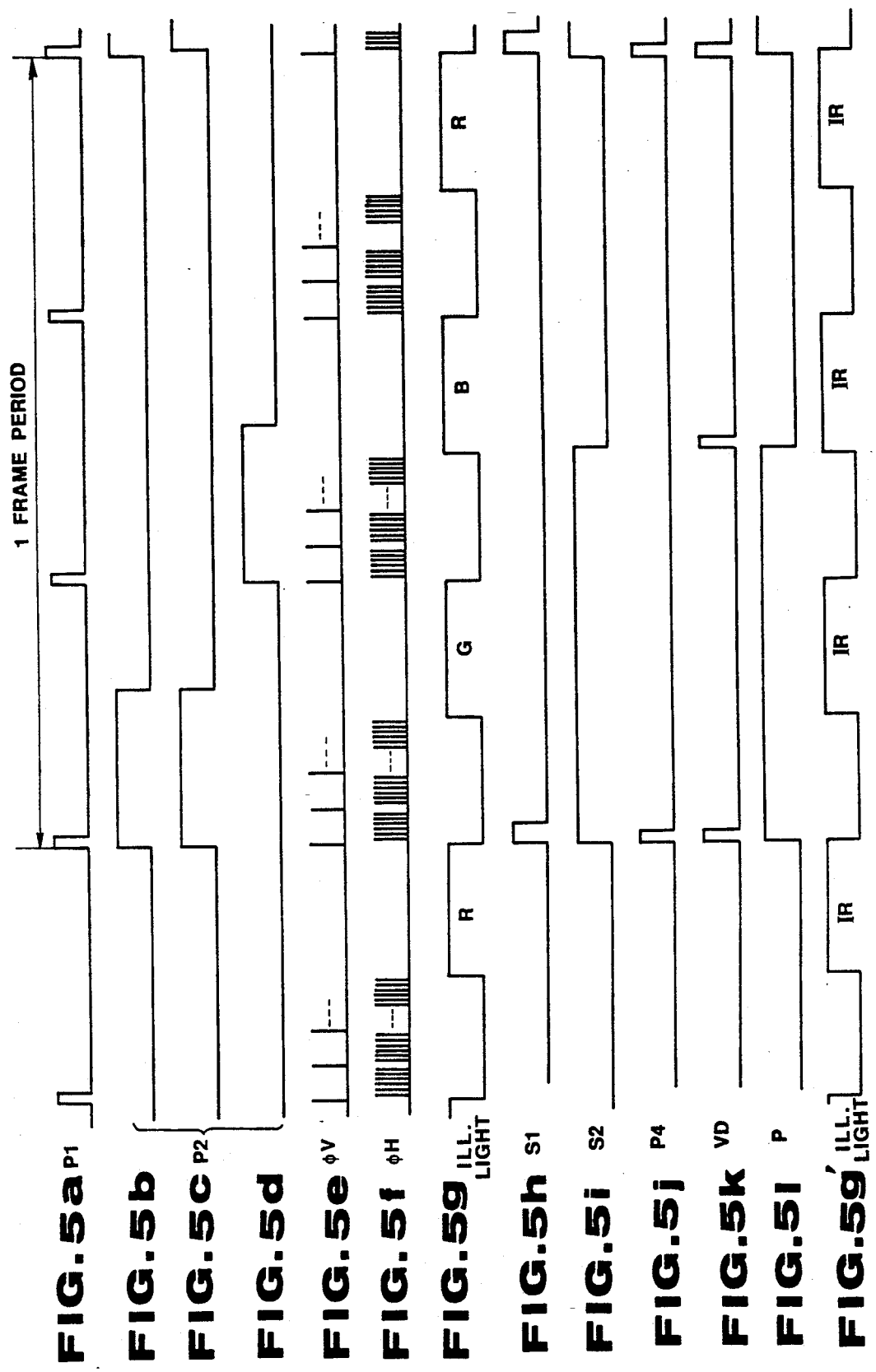

Meanwhile, in the same manner as in the case of the second light source 3B, the operation in the first light source 3A where the synchronizing signal VD is supplied from the CCU 5, as shown in FIG. 5, becomes almost the same way as the case of the second light source 3B.

In the first light source 3A, the rotary disk 24 provided with the transmitting parts 25 is fitted instead of the rotary filter 36 in the second light source 3B, and the infrared laser beam from the infrared laser beam source 8 is supplied as an illuminating light to the light guide 14 through the transmitting parts 25, 25 and 25. Accordingly, the illuminating light supplied to the light guide 14, shown in FIG. 5g, becomes an infrared laser beam represented by IR, as shown in FIG. 5g'. Each illuminating period of the infrared laser beam keeps the condition coinciding at each illuminating period as shown in FIG. 5g.

Also, the other signals in FIG. 5, such as S1, are similar to the case of the second light source 3B. Thus, the explanation of the other signals will be omitted.

Each output of a D/A converter 44 goes into an adding machine 59 and integrated by, for example, one frame period in an integrator 60 after the addition. Then, an exposure controlling signal (light intensity adjusting signal) is produced and transmitted to the communication circuit 32a and 32b in the light source 3A or 3B to which the light source connector 10 is connected through the communication line 20. The quantity of a diaphragm (blade) of the diaphragm means 28a or 28b includes a diaphragm blade (as shown in FIG. 4), and a motor for rotating and driving the diaphragm blade through the exposure controlling circuit 29a or 29b, and is controlled so that the quantity of illuminating light supplied to the light guide 14 can be adjusted by the control of the quantity of illuminating light. By this control, when the signal level of one frame period is too high, the quantity of light is decreased. On the other hand, when the signal level is too low, the quantity of light is increased so as to obtain a proper value of the signal level output on the side of the monitor 6 and to display a bright picture image which is easily diagnosed.

Further, in this embodiment, the rotary disk 24 and rotary filter 36 are synchronized with each other, rotated and driven. Also, the filters R, G and B and the transmitting parts 25 are synchronized with each other and face the optical path so that each signal obtained under the illumination through each transmitting part 25 is processed by the same signal processing as each signal obtained under the illumination through R, G and B filters. That is, the signal processing in the case where the first light source 3A is selected and used, is the same way as the signal processing in the case where the second light source 3B is selected and used.

Examples using the first embodiment formed as mentioned above will be explained as follows.

When an ordinary observation is carried out, the infrared rays electronic scope 2 is connected to the second light source 3B. The infrared rays electronic scope 2 feeds a signal imaged under the illuminating lights R, G and B in which colors are separated in a time series at the rotary filter 36 to the CCU 5 and the signal is displayed on the TV monitor 6 in the CCU 5 as ordinary R, G and B color picture images. The synchronizing signal VD of the R, G and B picture images is supplied from the CCU 5 to the system controller 30b of the second light source 3B through the light source connector 31b.

The system controller 30b makes the R, G and B rotary filters 36 synchronize with the R, G and B picture images by driving the motor 23b at the driving circuit 26b so as to synchronize the synchronizing signal VD of picture images R, G and B with a picture image read by the infrared rays electronic scope 2. Also, in the infrared rays electronic scope 2 in which the CCD 17 requiring a shading period is provided by this operation, the R, G and B color picture images can be obtained.

In the meantime, the infrared rays electronic scope 2 is connected to the input connector receiver 15a of the first light source 3A so that a picture image can be obtained by the illumination of the first light source 3A. The first light source 3A feeds infrared rays from the laser beam source 8 to the apparatus body through the light guide 7. The emitting light emitted from the end surface fixed to the mount 21 is converged by the lens 22a and led to the infrared rays electronic scope 2 intermittently by the rotary disk 24.

The infrared picture image is imaged at the CCU 5 in the same way as the ordinary R, G and B observation and displayed on the TV monitor 6. The vertical synchronizing signal VD used in this display is fed to the system controller 30a of the first light source 3A from the light source connector 31a. Based on the synchronizing signal VD, the motor 23a is driven at the driving circuit 26a and the rotary disk 24 is synchronized with the video signal of the CCU 5 and the infrared rays emitted from the infrared laser beam source 8 is synchronized with that which is read by the CCD 17 and led to the infrared rays electronic scope 2 from the output connector 15a as an intermittent light.

The infrared rays synchronized with the read of the CCD and intermittently illuminated is imaged as a clear picture image without a flare at the CCU 5 because the illuminating light is shaded at a reading period by the shading part of the rotary disk 24. Thus, the picture image is displayed on the TV monitor 6. The signal level imaged by the CCU 5 is fed to the first light source 3A from the output connector 15a through the communication line 20 of the infrared rays electronic scope 2 and the CCU 5.

The input picture image level signal is fed to the system controller 30a by the communication circuit 32a. The system controller 30a transmits the picture image level signal obtained from the communication circuit 32a to the exposure controlling circuit 29a, so that the system controller 30a can drive the diaphragm means 28a by the exposure controlling circuit 29a and adjust the quantity of the infrared laser beam to obtain a picture image of proper exposure.

According to the first embodiment, the most suitable light source can be used depending on an observing part or purpose. For example, if the observation with an infrared laser beam is not needed, an ordinary routine examination brings good results in that the entire system itself can be small because the first light source 3A emitting an infrared laser beam is removed. Further, not only an ordinary color picture image but also a picture image of an illuminating light of quite a narrow wavelength range in an electronic scope system which requires a shading period can be obtained. Thus, the observation of a pathologically changed portion under a mucous membrane of a living body and its infiltration range which cannot be observed by a diagnosis in an ordinary visible light range can be performed; thereby, improving the diagnosing ability.

Further, because the same illuminating optical system as used in an ordinary picture image is provided and an exposure controlling function can be also operated at illuminating infrared laser beams, a clear picture image can be easily compared with the ordinary observed image and can be obtained under the illumination of infrared laser beams. Also, even if a light source is switched to a light source from the other light source, the disorder of a picture image displayed on the TV monitor 6 can be controlled because the synchronizing signal VD is supplied to the light sources 3A and 3B from the CCU 5 and a timing for completing the illuminating period of the illuminating light is synchronized with the CCD reading period from the CCD 5.

For example, if a freeze picture image is produced before switching, a picture image imaged by the other light source can be displayed without having any disorder of the picture image when the freeze is removed after switching.

Figure 6:
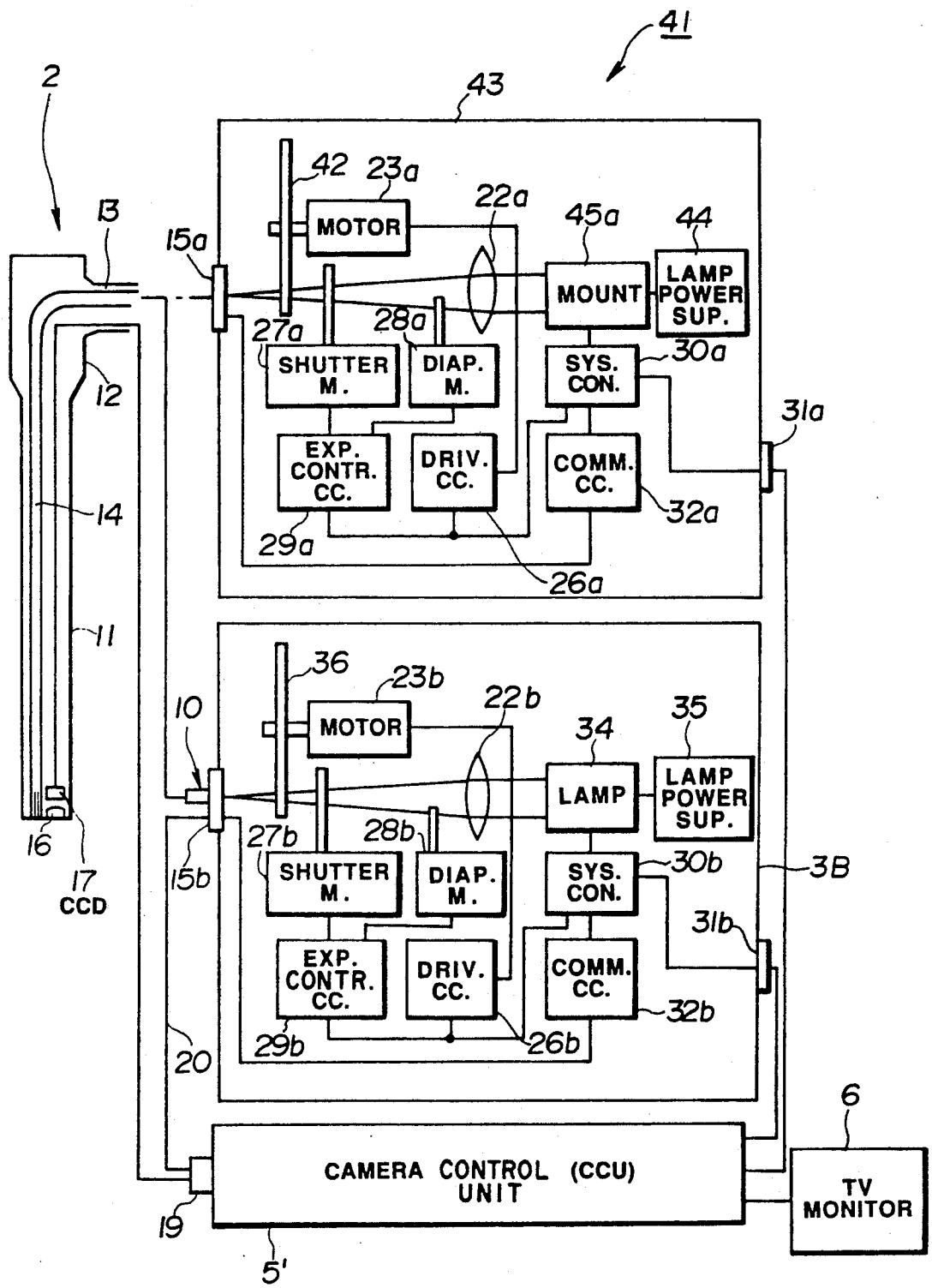

FIG. 6 shows an endoscope apparatus 41 in the second embodiment of the present invention.

Figure 7:
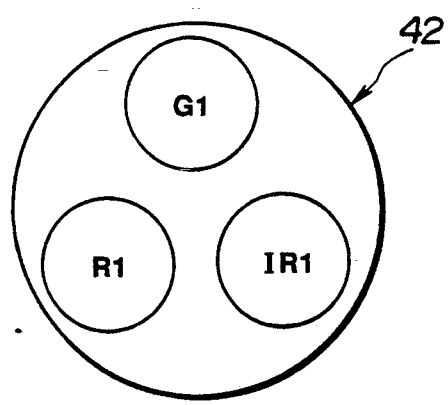
FIGS. 6 to 9 relate to the second embodiment of the present invention.
Figure 8:
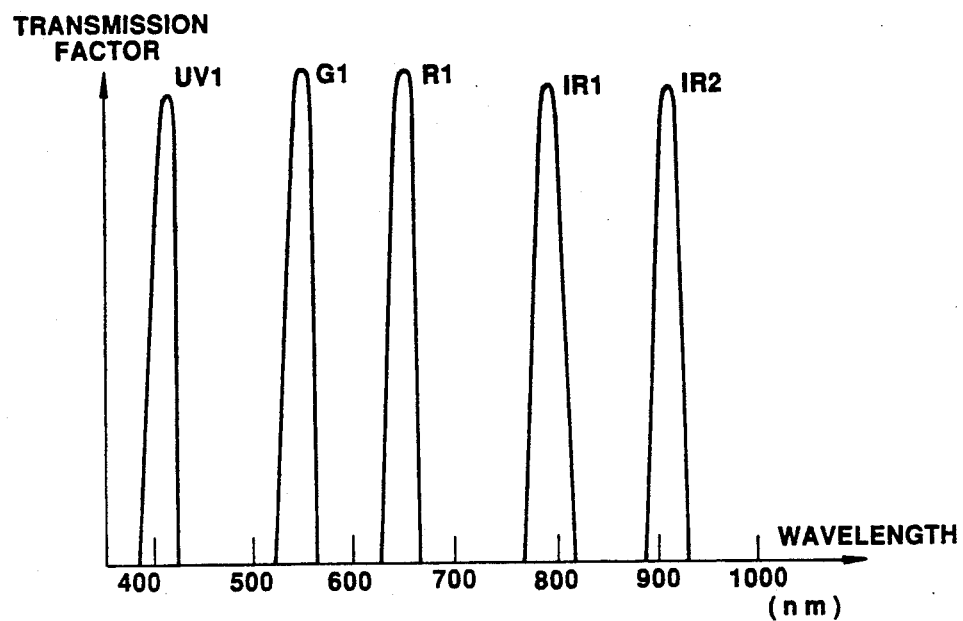

This second embodiment uses a rotary filter 42 to which filters G1, R1 and IR1 are attached as shown in FIG. 7, instead of the first light source 3A in the first embodiment shown in FIG. 1. Accordingly, the second embodiment does not contain the laser beam source 8. The filters G1, R1 and IR1 attached to the rotary filter 42 in a first light source 43 are adjusted to the transmission factor characteristics which pass green and red lights and infrared wavelength ranges in a narrow range, respectively, as shown in FIG. 8.

In the above mentioned first light source 43, an illuminating light of a lamp 45 which emits light by the electricity forms a lamp power supply 44 is converged by the lens 22a and becomes a light in narrow ranges of G1, R1 and IR1 through a rotary filter 42 and can supply light to the incident end surface of the light guide 14 fitted to the output connector receiver 15a.

The spectral characteristics of the above mentioned filters G1, R1 and IR1 are adjusted in the wavelength range where the spectral characteristics do not fluctuate due to the degree of saturation with oxygen in the hemoglobin, a pigment contained in blood. Also, the IR1 is adjusted in the wavelength range where the spectral characteristics fluctuate more conspicuously due to the degree of saturation with oxygen in hemoglobin. The picture image data obtained through each filter are processed and, for example, subtracted so that a picture image corresponding to the change of the density of hemoglobin and the degree of saturation with oxygen in hemoglobin can be displayed. The rotary filter 36 in the second light source 3B is shown in FIG. 3.

Figure 9:
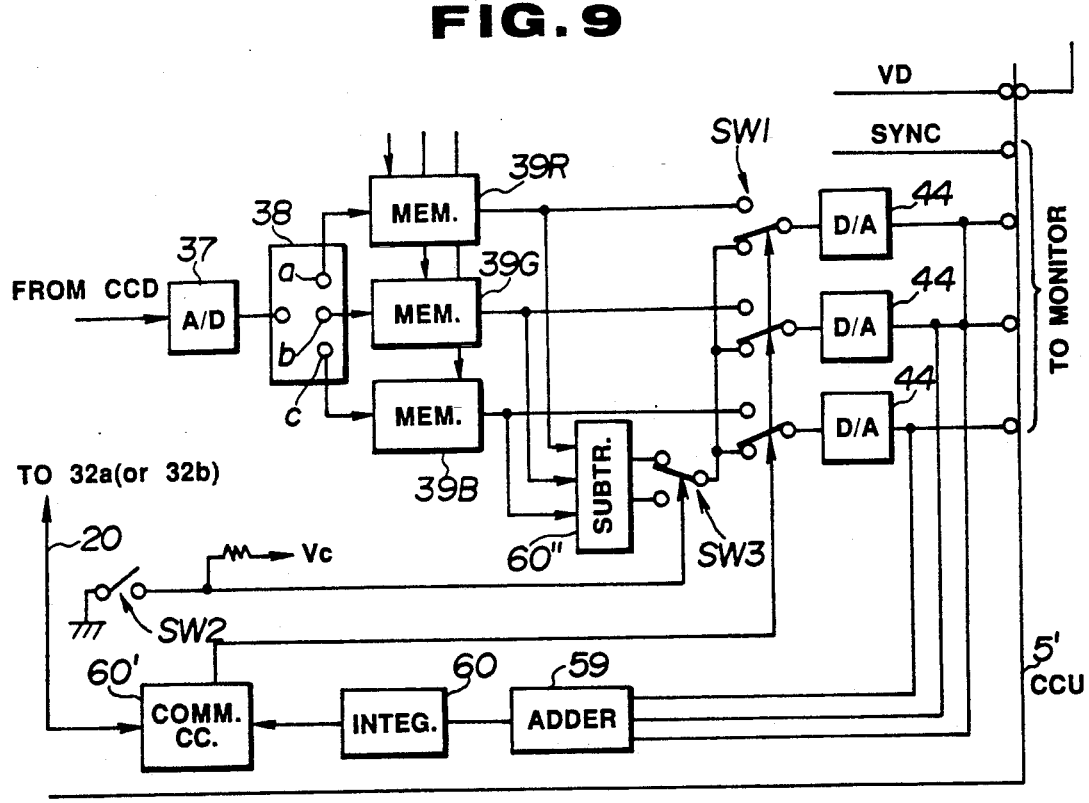

A rotary filter 42 formed as mentioned above makes possible the observation of the change of the density of hemoglobin and the degree of saturation with oxygen in hemoglobin in a mucous membrane of a living body by the difference of the density between wavelengths in which colors are separated. The structure of the main parts of a CCU 5' in this embodiment is shown in FIG. 9. The CCU 5' contains a communication circuit 60' added to the CCU 5 shown in FIG. 4. The communication circuit 60' communicates with a communication circuit 32a or 32b in the light source 43 or 3B to which the light source connector 10 is connected through the communication line 20 and controls the quantity of light of the light source 43 or 3B by the output of an integrator 60 and also switches the signal processing function of the CCU 5.

The output of the frame memories 39R, 39G and 39B is fed to a subtracter 60" and also to the D/A converter 44 through the switch SW1. The switching of this switch SW1 is controlled by a discriminating signal from the communication circuit 32a or 32b in the light source 43 or 3B electrically connected to the switch SW1 through a communication circuit 59. For example, in the case in which the light source 3B is connected to the switch, the output of the frame memories 39R, 39G and 39B is selected and a color picture image is displayed on the TV monitor 6.

Meanwhile, in the case of the light source 43, the output of the subtracter 60 subtracting the output of the frame memories 39R, 39G and 39B is selected and a picture image showing the change in the density of hemoglobin or the degree of saturation with oxygen in hemoglobin is displayed in response to a switch SW3 selected by a SW2 and a subtracting signal on the connected side. In this embodiment, the CCU 5' can process signals which are different between the case in which the first light source 43 is selected and the case in which the second light source 3B is selected. That is, the CCU 5' has a signal processing function corresponding to the two light sources 43 and 3B and selects a responsive signal processing function depending on the connection of the light source. (In the first embodiment, the case in which either light source 3A or 3B is used, a common signal processing function can be employed.)

The other structure is the same as shown in the first embodiment.

By the operation of the above mentioned structure, a color picture image illuminated by the second light source 3B in an ordinary observation and a functional picture image of hemoglobin illuminated by the first light source 43 can be obtained without providing a filter selection driving part in the main body.

Also, the first light source 43 for obtaining a functional picture image of hemoglobin a similar structure as the light source 3B for an ordinary routine examination. Thus, it is easy to remodel the ordinary light source, and a system of a special observation for obtaining a functional picture image of hemoglobin can be effectively provided at a reduced cost.

Figure 10:
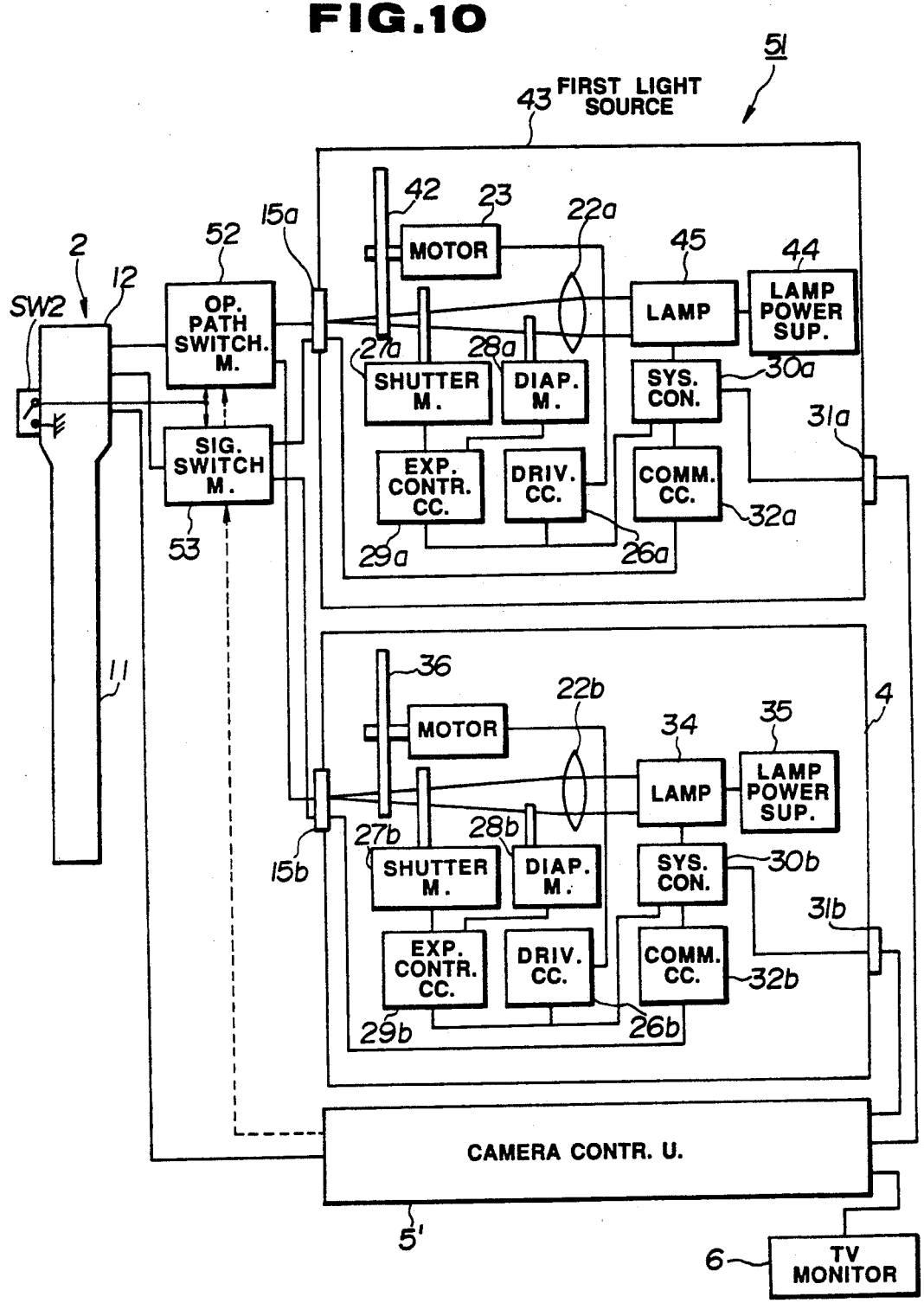
FIG. 10 is a formation diagram showing an endoscope apparatus of the third embodiment of the present invention.

FIG. 10 shows an endoscope apparatus 51 of the third embodiment of this invention.

In the third embodiment, the infrared rays electronic scope 2 shown in FIG. 6 is connected to the first light source 43 and second light source 3B through optical path switching means 52 and signal switching means 53, respectively.

That is, in this embodiment, the infrared rays electronic scope 2 is provided with the optical path switching means 52 for switching the optical path of a light guide which leads various illuminating lights from the light sources 43 and 3B to the infrared rays electronic scope 2 and the signal switching means 53 between the infrared rays electronic scope 2, and both of the second light source 3B and the first light source 43U.

This optical path switching means 52 includes of optical parts, such as a known mirror or prism, for switching illuminating light emitted from each of the first light source 43 and the second light source 3B to the infrared rays electronic scope 2. The signal switching means 53 switches an exposure controlling signal and a signal for synchronizing from the first light source 43 to the second light source 3B, and vice versa. The above mentioned switching of the optical path and signals is formed so as to be able to be switched by the switching switch SW2, which is provided in the operating part 12 of the infrared rays electronic scope 2. Alternatively, as shown by a broken line, the switch SW2 can be automatically switched by the signal from the CCU 5. The operation of this embodiment will be explained as follows.

When an ordinary color picture image is observed by the structure mentioned above, an illuminating light from a second light source 4 provided with the filters R, G and B in the rotary filter 36 by a switching switch (not illustrated) on the operating part 12 of the infrared rays electronic scope 2 is selected by the optical path switching means 52. At the same time, the exposure controlling and synchronizing signals from the CCU 5' are supplied to the second light source 3B for an ordinary observation by the signal switching means 53. Thus, this infrared rays electronic scope 2 is illuminated by illuminating lights R, G and B in a time series so that an ordinary color picture image can be obtained.

When a special picture image is selected by the infrared rays electronic scope 2, an illuminating light from the first light source 43 for a special picture image observation is selected by the optical path switching means 52 and the signal from the CCU 5' is supplied to the first light source 43 by the signal switching means 53, and then, a functional picture image of a mucous membrane of a living body is imaged by the infrared rays electronic scope 2.

According to the third embodiment, it is effective to improve the operability with the effects in the first and second embodiments because an ordinary color picture image and a special picture image can be switched by the switch SW 2 in a scope operating part. Also, a manual switching switch can be provided not only in the scope operating part but also at a foot switch or on a front panel. Further, the switch can be applied to an outside fitting camera.

The characteristics of the transmission factor of each filter attached to the rotary filter for obtaining a functional picture image is not limited to the above mentioned embodiment and can be used for all wavelength bands capable of imaging in the acceptance device of the electronic scope 2. For example, as shown in FIG. 8, the use of each wavelength range of R1, IR1 and IR2 can image the change of the degree of saturation with oxygen in hemoglobin. Also, a subject is illuminated by an illuminating light in an ultraviolet range, such as UV1, and imaged with the images of the other wavelength ranges so that the microstructure and micro red coloring of a mucous membrane of a living body can be imaged in contrast with the other parts.

Figure 11:
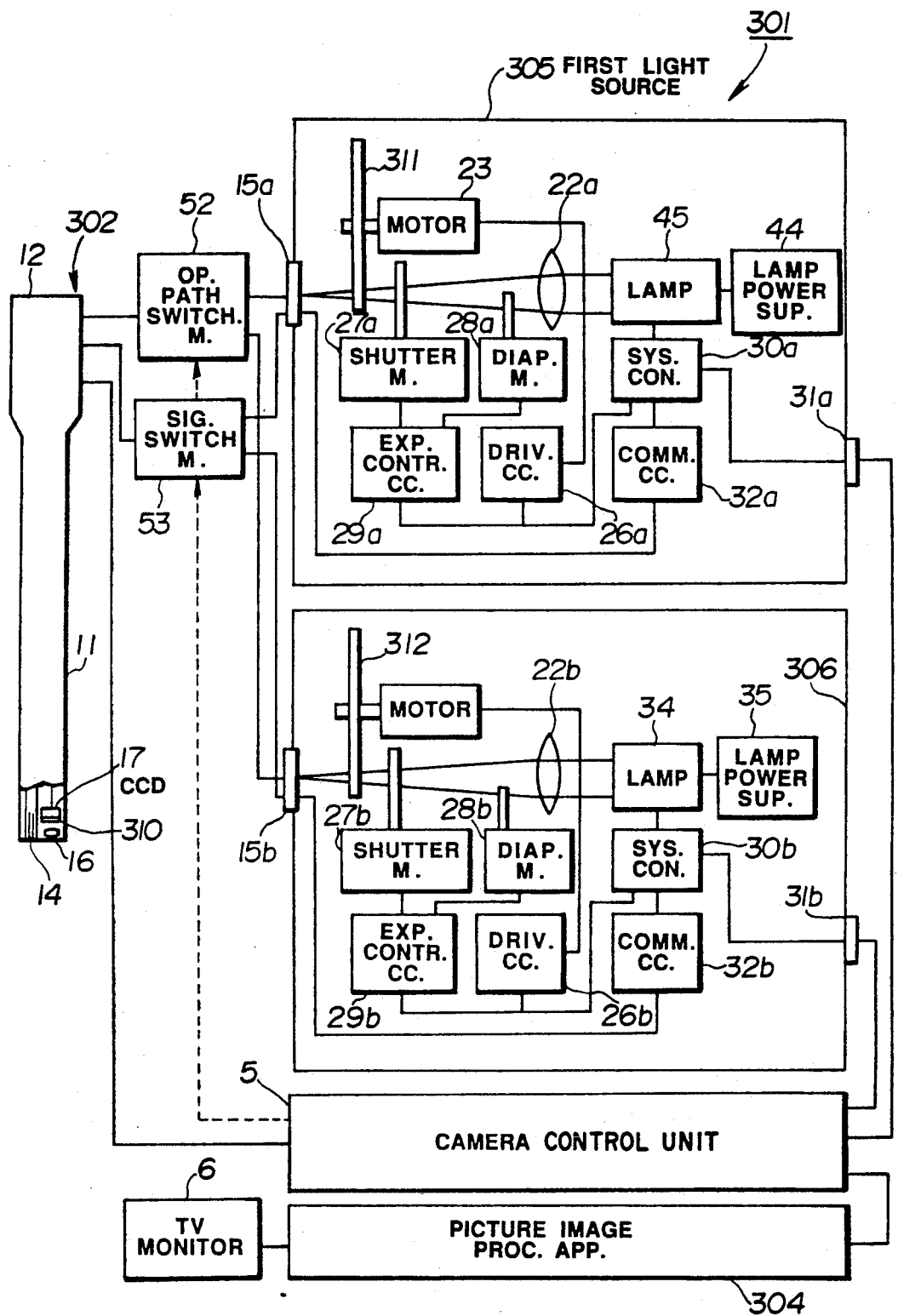
FIG. 11 is a formation diagram showing the endoscope apparatus of a first modification of the third embodiment.

FIG. 11 shows a first modification of an endoscope apparatus 301 in the third embodiment shown in FIG. 10. The endoscope apparatus 301 includes an infrared rays electronic scope 302 of the simultaneous type provided with a mosaic color separating filter 310, which is a complementary type, before the imaging surface of the CCD 17, the CCU 5 for converting a picture signal from the infrared rays electronic scope 302 into a standard TV signal, a picture image processing apparatus 304 most suitably for processing signals in every kind of information of a living body function, a first light source 305 and a second light source 306 for supplying a first and second illuminating lights to the infrared rays electronic scope 302, respectively, and the TV monitor 6 for displaying the output signal of the picture image processing apparatus 304.

Figure 12:
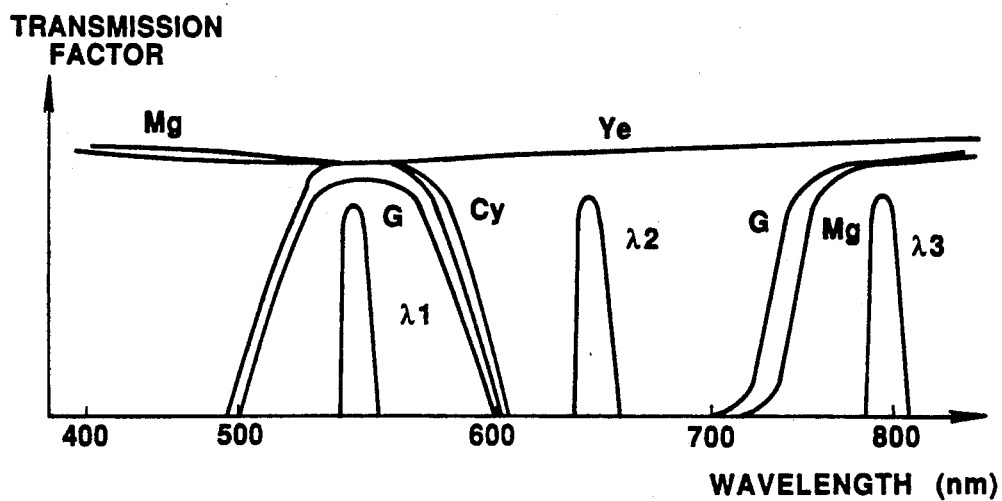
FIG. 12 is a characteristic diagram showing transmission factor characteristics of color separating filters or the like used in an endoscope apparatus in FIG. 11.

In the above mentioned infrared rays electronic endoscope 302, a color separating filter 310 is provided before the CCD 17 in the infrared rays electronic endoscope 2 in FIG. 10. In the color separating filter 310, color transmission filters of a complementary colors type having the transmission characteristics of Mg, G, Ye and Cy, as shown in FIG. 12, are arranged in a mosaic pattern. Also, a rotary filter 311, shown in FIG. 13a, is used in a first light source 305 instead of the rotary filter 42 in the first light source 43 in FIG. 10.

Figure 13A:
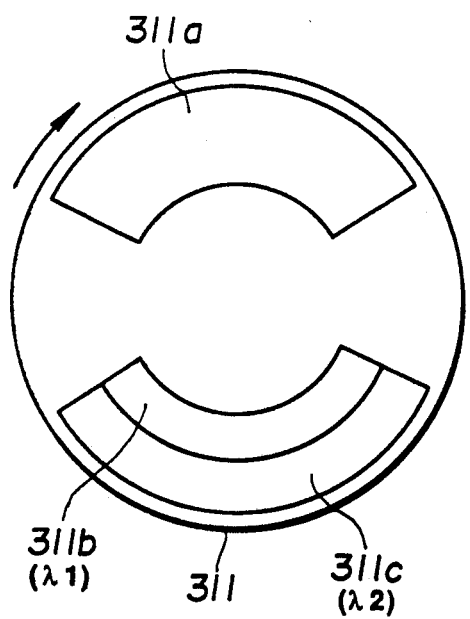
FIG. 13 is an explanatory view of a rotary filter used in first and second light sources.

In this rotary filter 311, a sectorial infrared cut filter 311a and filters 311b and 311c having two different transmission characteristics in the sector part facing the infrared cut filter 311a are provided in the radius direction as shown in FIG. 13a. The rotary filter 311 limits the emitting light wavelength of a lamp 45 and supplies light to the light guide 14 in the infrared rays electronic scope 302. The above mentioned filters 311b and 311c have transmission characteristics (represented by λ1 and λ2) for transmitting the wavelengths 570 nm and 650 nm in each narrow band shown in FIG. 12.

Figure 13B:
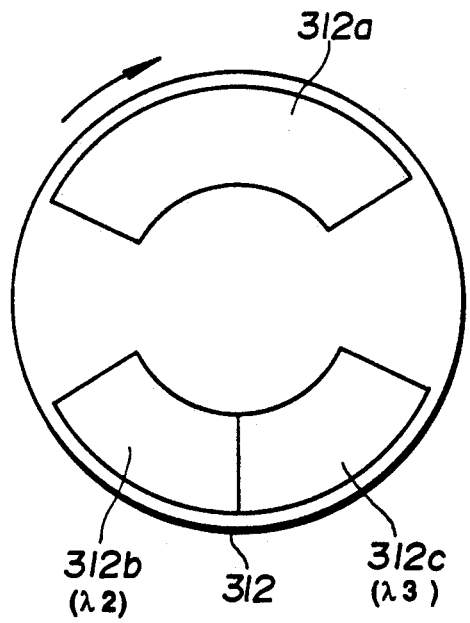

Also, a rotary filter 312, shown in FIG. 13b, is used in the second light source 306 instead of the rotary filter 36 in the second light source 4 in FIG. 10. In the rotary filter 312, a sectorial infrared cut filter 312a, and filters 312b and 312c having two different transmission characteristics in the sector part of the rotary filter facing the infrared cut filter 312a are provided as shown in FIG. 13b. The rotary filter 312 limits the emitting light wavelength of a lamp 34 and supplies it to the light guide 14 in the infrared rays electronic scope 302. The filters 312b and 312c of the rotary filter 312 have transmission characteristics (represented by λ2 and λ3) for transmitting the wavelengths 650 nm and 790 nm in each narrow band shown in FIG. 12.

The above mentioned rotary filters 311 and 312 are synchronized with the read timing of the infrared rays electronic scope 302 and rotatively driven. Accordingly, the infrared cut filter 311a in the rotary filter 311 in FIG. 13a is synchronized with the infrared cut filter 312a in the rotary filter 312 in FIG. 13b and these filters are rotatively driven. Also, the filter 311b (or 311c) is synchronized with the two filters 312b and 312c and rotatively driven.

Further, in the case when the rotary filter 311 is selected for use, a CCD driving signal is generated twice during the rotary filter 311 being rotated once, while, in the case when the rotary filter 312 is selected for use, a CCD driving circuit (for example, see reference numeral 36 in FIG. 4) is controlled so that a CCD driving signal can be generated three times during the rotary filter 312 being rotated once.

In other words, in the case when the rotary filter 312 is selected for use, one extra driving signal is generated after the illuminating period of the filter 312b, as compared with the case when the rotary filter 311 is selected for use. In this embodiment, a CCD which does not require a shading period (for preventing smear), such as an interline transmission type, is used as the CCD 17 at reading. (When a shading part is provided between the filters 312b and 312c, a line transmission type CCD which requires a shading period can be used).

The other structure is the same as the structure shown in FIG. 10. The operation of the apparatus 301 is explained as follows.

When the first light source 305 is selected, the rotary filter 311 is synchronized with the read of the infrared rays electronic scope 302 and rotated. When the infrared cut filter 311a is inserted into the optical path, an ordinary visible color picture image can be imaged. In the subsequent timing when the filters 311b and 311c are inserted into the optical path, the picture images in narrow band wavelengths 570 nm and 650 nm are imaged as G and R signals processed by the color separating filter 310, respectively.

A color picture image is λ-corrected for an ordinary visible color observation and supplied to the picture image processing apparatus 304 by the timing in which the infrared cut filter 311a is inserted into the optical path because the rotary filter 311 is synchronized with the timing of the signal processing of the CCU 5, and rotated and driven.

In the meantime, when the filters 311b and 311c are inserted into the optical path, a picture image in the narrow band wavelengths 570 nm and 650 nm is imaged and fed to the picture processing apparatus 304 as a G or R picture image with the characteristic of $\lambda=1$. The picture image processing apparatus 304 temporarily stores the ordinary visible color picture image in a memory under ordinary illumination of the first light source 305 in which the infrared cut filter 311a is inserted into the optical path. Further, in order to emphasize the distribution of blood quantity in a living body for the picture signal in the narrow band wavelengths in which $\lambda$-correction is removed, a level difference between two picture signals in narrow band wavelengths is calculated by the subtracting circuit or the like and the calculated level difference is simultaneously displayed on the TV monitor 6 with the above mentioned ordinary visible color picture image which is temporarily stored.

Next, when the second light source 306 is switched, the CCU 5 supplies an ordinary visible color picture image which is $\lambda$-corrected to the picture image processing apparatus 304 in the timing by which the infrared cut filter 312a is inserted into the optical path as the same way as explained in the case of the first light source 305, and then, the image is temporarily stored in a memory in the picture image processing apparatus 304.

Picture images in narrow band wavelengths $\lambda 2$ and $\lambda 3$ are obtained as the signals of R and G picture images, respectively, by the timing in which the filters 312b and 312c of the rotary filter 312 are inserted into the optical path. Then, the CCU 5 supplies the picture images in which the $\lambda$-correction is removed to the picture image processing apparatus 304. As explained in the case of the first light source 305, the picture image processing apparatus 304 calculates a level difference between two picture images and emphasizes the change in the degree of saturation with oxygen in hemoglobin in a living body. Then, the level difference is simultaneously displayed on the TV monitor 6 with the ordinary visible color picture image temporarily stored.

By the apparatus 301, the ordinary observation of the distribution of the blood quantity in a mucous membrane of a living body can be performed so that an emphasized processing picture image for the change in the degree of saturation with oxygen in hemoglobin can be simultaneously observed on the TV monitor 6. Thus, the apparatus is effective in improving a diagnostic ability.

Also, a plurality of monitors can display images without displaying on the TV monitor 6 simultaneously. Also, the output of the picture image processing apparatus 304 can be switched between the ordinary visible color picture image and the emphasized processing picture image and displayed.

Figure 14:
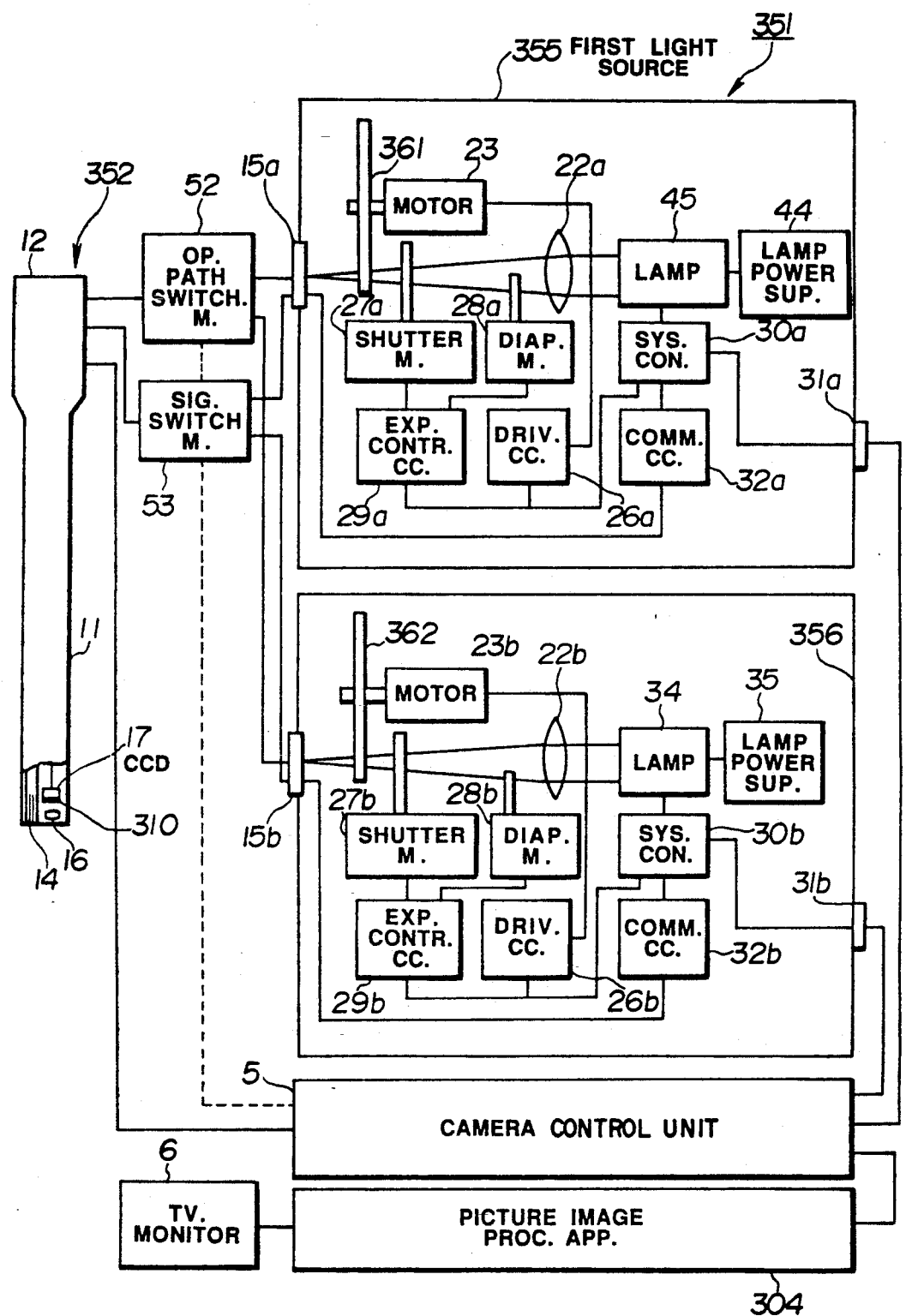
FIG. 14 is a formation diagram of an endoscope apparatus showing a second modification of the third embodiment.

FIG. 14 shows the endoscope apparatus 351, the second modification of the third embodiment. The endoscope apparatus 351 consists of an infrared rays electronic scope 352 having a mosaic color separating filter 360 of a complementary type arranged before the imaging surface of the CCD 17, the CCU 5 converting a picture signal from the infrared rays electronic scope 352 into a standard TV signal, a picture image processing apparatus 304 most suitably processing signals in every kind of information of a living body function, a first light source 355 and a second light source 356 supplying a first and second illuminating lights to the infrared rays electronic scope 352, respectively, and the TV monitor 6 displaying the output signal of the picture image processing apparatus 304.

In the above mentioned infrared rays electronic endoscope 352, a color separating filter 360 is provided before the CCD 17 in the infrared rays electronic endoscope 2 in FIG. 10. In the color separating filter 360, color transmission filters having the transmission characteristics of Mg, G, Ye and Cy as shown in FIG. 15 and also having transmission characteristics in the infrared rays range are arranged in a mosaic pattern. Also, a rotary filter 361, shown in FIG. 16a, is used in a first light source 305 instead of the rotary filter 42 in the first light source 43 in FIG. 10.

In this rotary filter 361, a sectorial infrared cut filter 361a and many filters of 361b, 361c and 361d having three different transmission characteristics in the sector parts facing the infrared cut filter 361a are provided. The rotary filter 361 limits the wavelength of the light emitted from a lamp 45 and supplies the light to the light guide 14 of the infrared rays electronic scope 352. The above mentioned filters 361b, 361c and 361d have transmission characteristics (represented by $\lambda 1$, $\lambda 2$ and $\lambda 3$) for transmitting the wavelengths 570 nm and 650 nm in each narrow band shown in FIG. 15.

Also, a rotary filter 362, shown in FIG. 16b, is used in the second light source 356 instead of the rotary filter 36 in the second light source 4 in FIG. 10. In the rotary filter 362b, a sectorial infrared cut filter 362a and a rotary filter 362b having transmission characteristics in the sector part facing the infrared cut filter 361a are provided as shown in FIG. 16b. The rotary filter 362 limits the wavelength of the light emitted from a lamp 34 and supplies light to the light guide 14 of the infrared rays electronic scope 302. The filter 362b of the rotary filter 362 has transmission characteristics (represented by $\lambda 0$) for transmitting short wavelengths, for example, 450 nm and below in FIG. 14.

The above mentioned rotary filters 361 and 362 are synchronized with the read timing of the infrared rays electronic scope 352 and rotatively driven.

The operation of the apparatus 351 will be explained as follows. When the first light source 355 is selected, the rotary filter 361 is synchronized with the reading of the infrared rays electronic scope 352 and rotated. When the infrared cut filter 361a is inserted into the optical path, an ordinary visible color picture image can be imaged. The CCU 5 supplies a $\lambda$-corrected ordinary visible color picture image to the picture image processing apparatus 304 and the picture image is temporarily stored in a memory in the picture image processing apparatus 304.

When the filters 361b, 361c and 361d are inserted into the optical path, the picture images in three kinds of narrow band wavelengths $\lambda 1$, $\lambda 2$ and $\lambda 3$ are obtained and the CCU 5 supplies the picture images in which $\lambda$-correction is removed to the picture image processing apparatus 304. The picture image processing apparatus 304 calculates the level difference among the three kinds of picture images and calculates the change of the degree of saturation with oxygen in hemoglobin in a living body or the change of ICG pigment density in a mucous membrane when ICG is injected intravenously.

Meanwhile, when the second light source 356 is switched, as explained in the case of the first light source 355, the CCU 5 supplies the λ-corrected ordinary visible color picture image to the picture image processing apparatus 304 in the timing in which the infrared cut filter 362a of the rotary filter 362 is inserted into the optical path and the picture image is temporarily stored in a memory in the picture image processing apparatus 304.

Then, when the filter 362b is inserted into the optical path, a light on the short wavelength side is applied to a living body. Since the light on the short wavelength side has an effect for exciting the fluorescent material sprayed on or injected into a living body intravenously, the infrared rays electronic scope 352 having sensitivity on the long wavelength side can image the fluorescence. Further, an observation can be carried out without spraying or injecting with a fluorescent material intravenously in order to image the fluorescence emitted from a living body itself.

In the picture image processing apparatus 304, when the first light source 355 is selected as mentioned above and the infrared cut filter 361a is inserted into the optical path, an ordinary visible color picture image is temporarily stored in a memory and the level difference among the picture signals obtained when the filters 361b, 361c and 361d are inserted into the optical path and then, the change of the degree of saturation with oxygen in hemoglobin in a living body or the change of the ICG pigment density in a mucous membrane at injecting ICG intravenously is calculated. Thus, the change of the degree of saturation with oxygen in hemoglobin or of the ICG pigment density is displayed on the TV monitor 6 with or without an ordinary visible color picture image depending on an operator's selective operation.

When the second light source 356 is selected and the infrared cut filter 362a is inserted into the optical path, the picture image processing apparatus 304 temporarily stores an ordinary visible color picture image in a memory and calculates a fluorescent level of a living body using picture signals R and G on the R and G long wavelength side which are obtained when the filter 362b is inserted into the optical path so as to display the fluorescent level on the TV monitor 6 with or without an ordinary visible color picture image.

By the apparatus 351, an ordinary visible color picture image and a living body functional image can be observed simultaneously, as in the first modification, and in addition, the circulation speed of the blood; that is, blood flow speed can be observed by time series changes of the pigment density in a blood vessel by an intravenous injection of the ICG pigment.

Also, it is effective that the fluorescence of a living body can be observed by the irradiation of light on the short wavelength side to a living body, and the ability for recognizing a pathologically changed part can be improved by the observation of the distribution change of the fluorescent material taken in a pathologically changed part in a mucous membrane.

Further, the fluorescence emitted from a reduced form of pyridine nucleotide (NADH), one of oxygen density indicating materials in living body tissue, can be observed and the increase and decrease of the quantity of oxygen in a mucous membrane in a living body can be estimated.

Also, the luminance, saturation and hue of a visible color picture image can be emphasized on the basis of the picture image information processed as a functional picture image of a living body and the outline of a part having a variety of changes can be composed.

Figure 17:
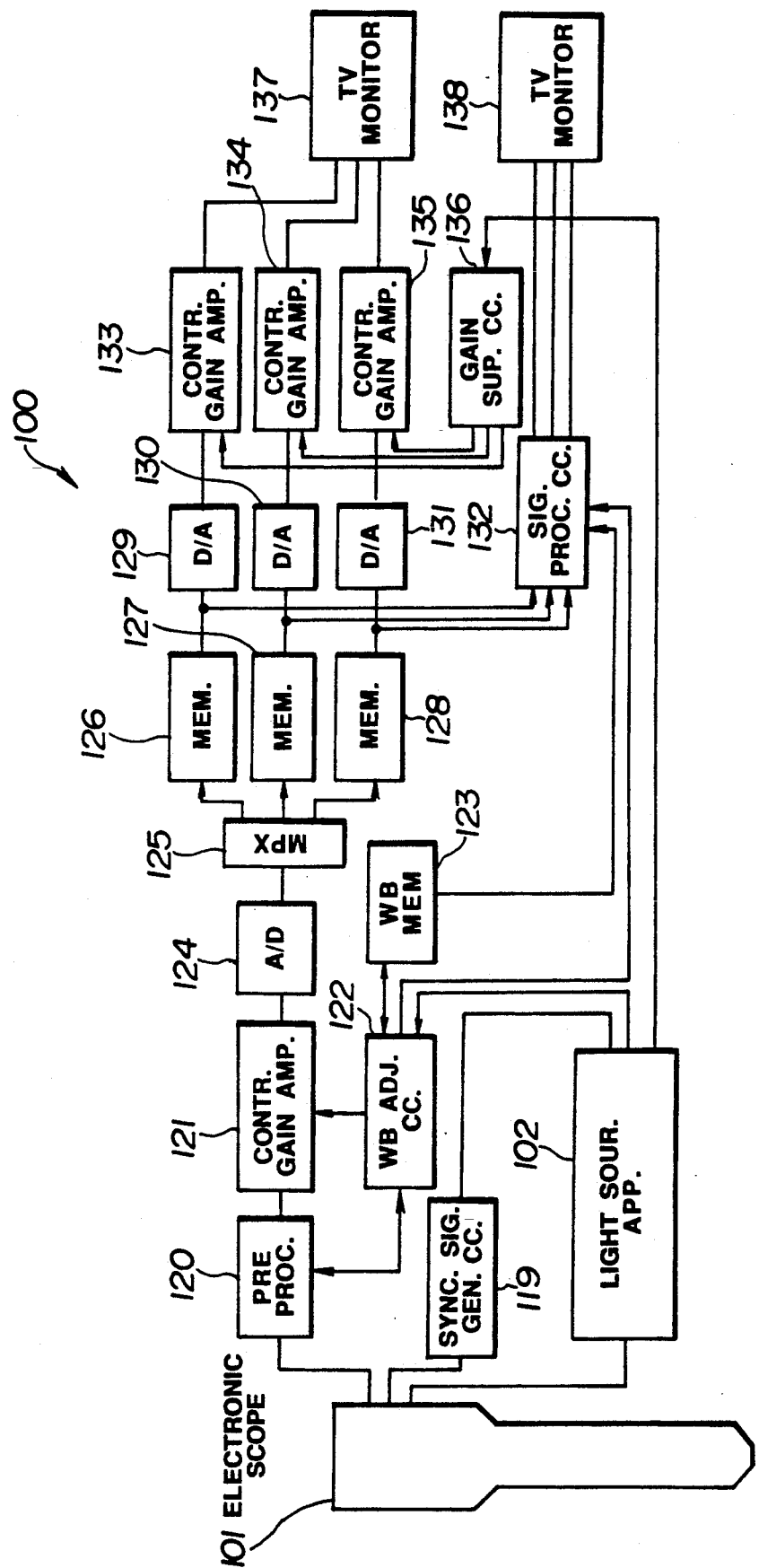
FIG. 17 is a formation diagram of an endoscope apparatus provided with a function for correcting each picture signal level when a subject is imaged.
Figure 18:
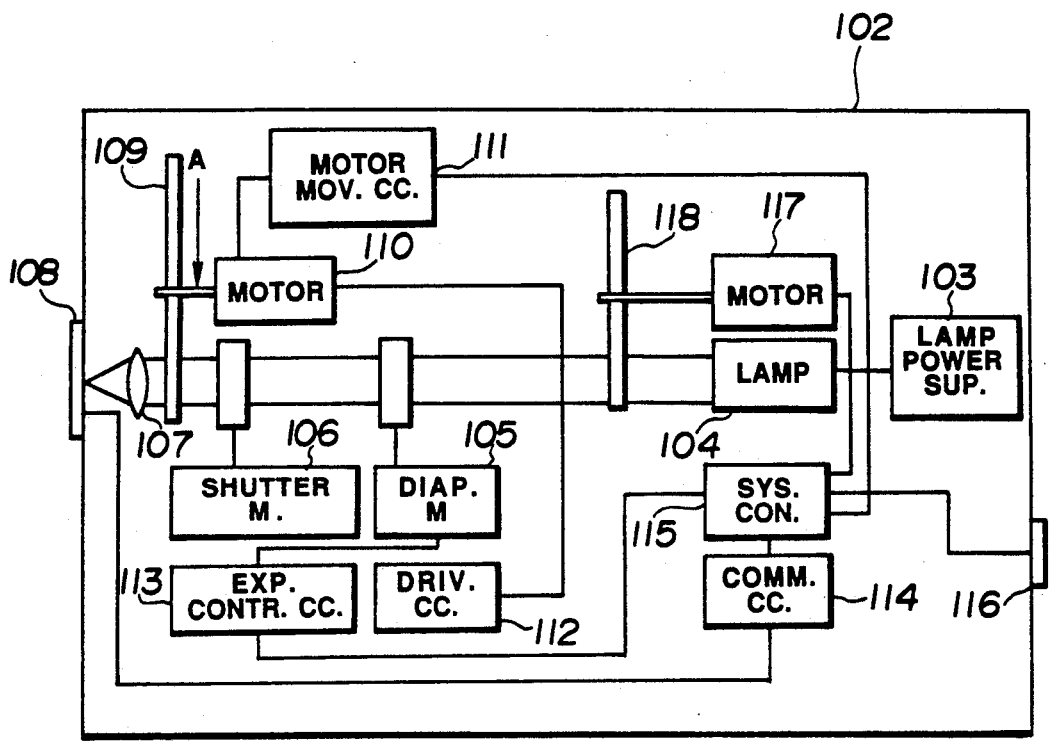
FIG. 18 is a formation diagram of a light source apparatus in FIG. 17.

FIG. 17 shows an endoscope apparatus 100 which illuminates a subject to make the picture signal level of each R, G and B almost the same level when the subject is imaged and which can increase a dynamic range of a color signal. An illuminating light is transmitted to an electronic scope 101 which is inserted into a living body and performs observation through a light guide (not illustrated) for leading light from a light source apparatus 102. The light source apparatus 102 is composed as shown in FIG. 18. A lamp 104 emits a light in a wide wavelength band including an ultraviolet range, visible light range and infrared range by the electricity supplied from the lamp power supply 103.

Figure 19:
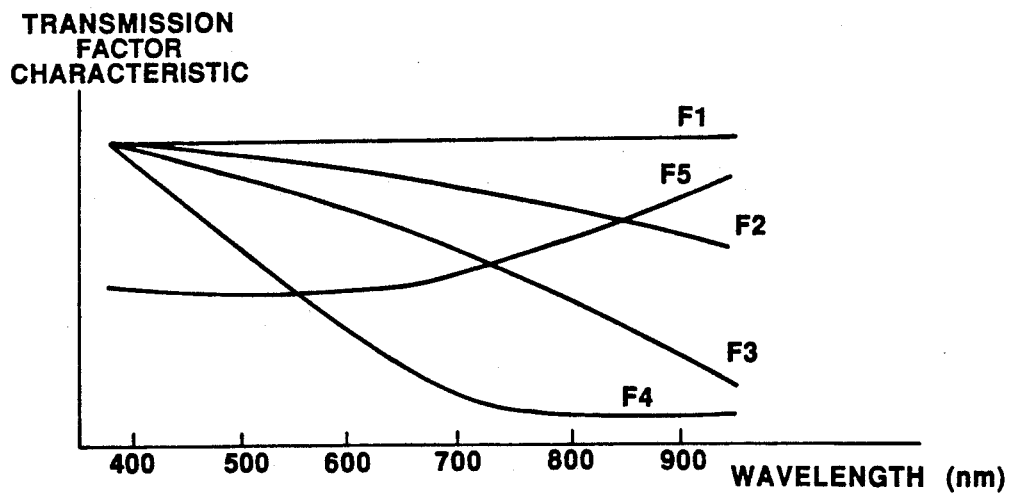
FIG. 19 is a front view showing a filter turret used in a light source apparatus in FIG. 17.
Figure 20:
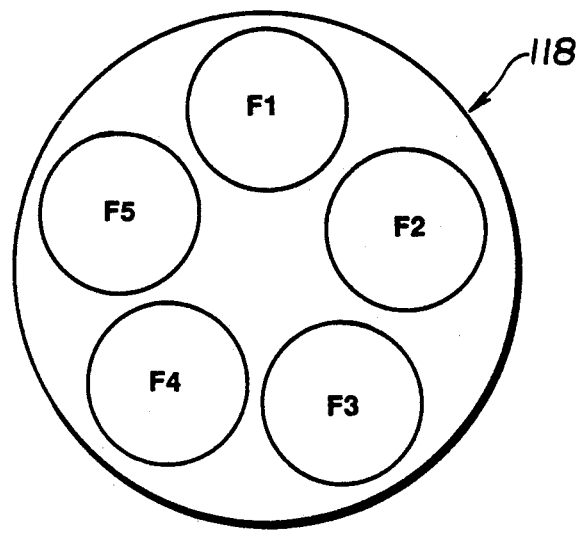
FIG. 20 is a front view showing a rotary filter used in a light source apparatus in FIG. 17.

The spectral characteristics of the light in wide wavelength bands emitted from the lamp 104 are adjusted by a filter turret 118 in which filters F1-F5 having characteristics, shown in FIG. 19, are arranged (shown in FIG. 20). The filter turret 118 is rotated by a motor 117 and can change the spectral characteristics of the lamp 104 using the filters F1-F5 which have various characteristics. The motor 17 is controlled by a system controller 115.

The system controller 115 transmits a picture signal level obtained through a communication circuit 114 to an exposure controlling circuit 113 so that diaphragm means 105 is driven by an exposure controlling circuit 29 and the quantity of illuminating light is adjusted.

In the illuminating light having its spectral characteristics changed by the filter turret 118, the quantity of the illuminating light is adjusted by the diaphragm means 105 to obtain suitable quantity of the light and separated colors in time series by the rotation of a rotary filter 109 by a motor 110 controlled by a driving circuit 112 through shutter means 106 making the illuminating light ON and OFF.

Figure 21:
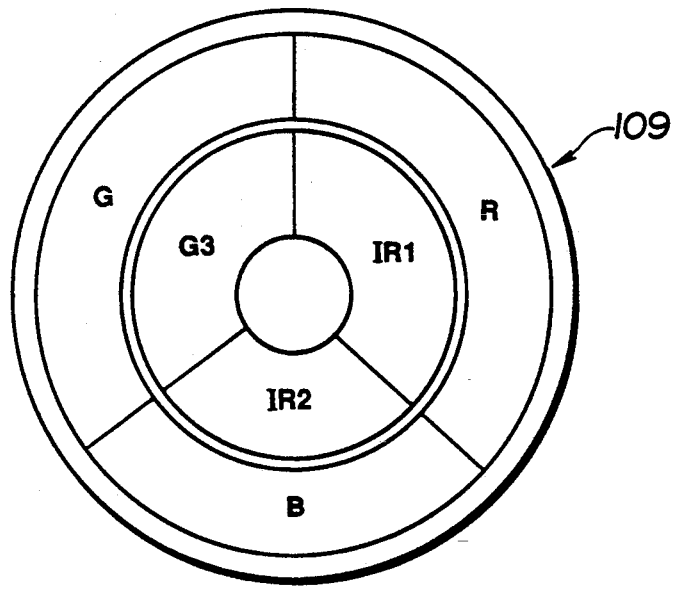
FIG. 21 is a characteristic diagram showing transmission factor characteristics of a filter fitted to a filter turret in FIG. 17.

The structure of the rotary filter 109 is shown in FIG. 21. Combinations of two filters are arranged in the circumference direction on the filter 109. For an ordinary observation, colors are separated by the filters R, G and B on the outside. When it is desired to observe and measure the functional information of a living body, necessary color separation is performed by inserting an inside filter of the rotary filter 109 into the optical path. The rotary filter 109 can be adjusted in either condition in which the filter 109 is slightly inserted into the optical path as shown in FIG. 18, or the filter 109 is more deeply inserted than the above condition shown by the arrow A.

The illuminating light separated by the rotary filter 109 is converted by a lens 107 and connected to an electronic scope 101 by a scope connector 108 to illuminate the inside of a living body. Since the inside of a living body usually appears as an extremely red tone, the red color is almost saturated when a white balance is adopted by a white color as in the ordinary white balance and when the inside of the living body is observed. (Therefore, in this condition, it is difficult to recognize a subtle distinctive part in red.)

Thus, the white balance is adopted for a white color on the unevenness of the light guide, CCD and signal processing system by the characteristics of the F1 among the filters of the filter turret 118. After that, the filters F1-F5 of the filter turret 118 is selected by a system controller 115 so that the spectral characteristics of the illuminating light has each equal light color reflected from the living body and has no saturated color (or near saturated color). Then, the selected data is sent from a light source connector 116.

Among the filter characteristics in FIG. 19, the F1 has the characteristics for keeping spectral characteristics of the light source unchanged in order to reproduce ordinary colors; F2-F4 have the characteristics for selecting the most suitable characteristics; by a living body characteristics and F5 has the characteristics for using when dyeing, such as Methylene Blue.

Before the examination, a white balance is adjusted for a white board by the illuminating light through the characteristic filter of F1 among the filters attached to the filter turret 118 and the electronic scope 101 is inserted into the living body cavity and a video signal is obtained. The obtained video signal is processed in a pre-processing circuit 120. Then, a color signal having an extremely high color signal level and a saturated signal or having a low color signal level and a poor S/N among signal levels in a WB adjusting circuit 122 is calculated and transmitted to the system controller 115 through the light source connector 116. The system controller 115 selects the filter of the filter turret 118, so as not to be saturated at an extremely high video signal level not to be too low. Thus, the system controller 115 selects the filter to make the spectral characteristics of the illuminating light the most suitable for the subject.

The picture signal read from the electronic scope 101 is processed in the pre-processing circuit 120. In a control gain amplifier 121, when a white balance is adjusted by a white board for the first time, a level difference among color signals is calculated in the WB adjusting circuit 122 and stored in a WB memory 123. Based on this data, the light guide, CCD the and signal processing system are corrected.

In the meantime, since the mucous membrane in a living body appears red tone, a large difference of the level among color signals is produced so that the electronic scope 101 can obtain a picture image having adjusted levels of each color signal by changing the spectral characteristics of the illuminating light and illuminating the membrane by the filter turret 118. The obtained picture image is processed in the pre-processing circuit 120 and fed to the control gain amplifier 121.

The level of the picture signal separated each color is adjusted by the white balance data stored in the WB memory 123 by a white board and converted into a digital signal in an A/D converter 124. After that, the picture signal read in time series is synchronized in memories 126, 127 and 128 in every picture signal which is separated colors in a multiplexer 125.

In the picture signal level supplied from each memory, the red tone of the living body appears a white tone as a whole because the spectral characteristics of the illuminating light is changed and each color signal level is equal. Therefore, each color signal is not saturated and a good S/N picture signal is fed into the signal processing circuit 132. When a calculation among picture images is performed, selected filter information is fed from the WB adjusting circuit 122 to the signal processing circuit 132 and used as a corrected data for the calculation to change the spectral characteristics of the illuminating light. The processed result is displayed on a TV monitor 138.

Meanwhile, the picture signal for observation is changed into an analog signal in the memories 126, 127 and 128 to D/A converters 129, 130 and 131. Then, in the control gain amplifiers 133, 134 and 135, each picture signal level is changed by an adjusted gain in a gain supplying circuit 136 to correct the characteristics of the filter of the selected filter turret 118. The picture signal obtained as a white tone by an illuminating light in the gain control amplifiers 133, 134 and 135 is displayed on a TV monitor 137 in which actual tone is corrected.

Also, high quality calculation among picture images can be processed even when the spectral characteristics of a subject has the extremely different level among video signals at calculating among picture images because the inside filters of the rotary filter 109 is selected to image the functional information of a living body and the most suitable filter of the filter turret 118 is selected in the WB adjusting circuit 122.

When an observing part is restricted or when a higher quality observation is required, the filter of the filter turret 118 is selected by a chart provided with the same spectral characteristics as the subject and a white balance is adjusted by the WB adjusting circuit 122 and then, the data is stored in the WB memory 123. Based on the stored data, the image is corrected in the signal processing circuit 132, so that the image can be corrected by each filter provided in the filter turret 118 so that high quality correction can be carried out.

When there is not much difference in average colors among subjects, the numerical aperture of the rotary filter 109 is adjusted so as to make the video signal level of each color almost equal by the chart having the same average tone as the subject and each color signal level can be adjusted to make the image the same color as the subject in the control gain amplifiers 133, 134 and 135.

Also, in a synchronizing signal generating circuit 119, the electronic scope 101 and the light source 102 are connected and the timing of the illumination in a time series is synchronized with the timing of the signal processing system.

In the above mentioned structure, the white balance is adopted not only in the signal processing system containing the CCD as in the prior art but also the illumination considering the average color of the subject is applied so that each color signal can be correctly expressed in the mucous membrane of which the average color is near red or even in the mucous membrane which is dyed by various pigments. Thus, when the living body functional information is calculated, very small differences among color signals can be correctly calculated so that it is effective so that the diagnostic ability can be improved.

Also, this application is not only restricted to the frame sequential system but can also be performed by the simultaneous system. In addition, this application can be carried out by a fiberscope and an outside fitted camera.

Figure 22:
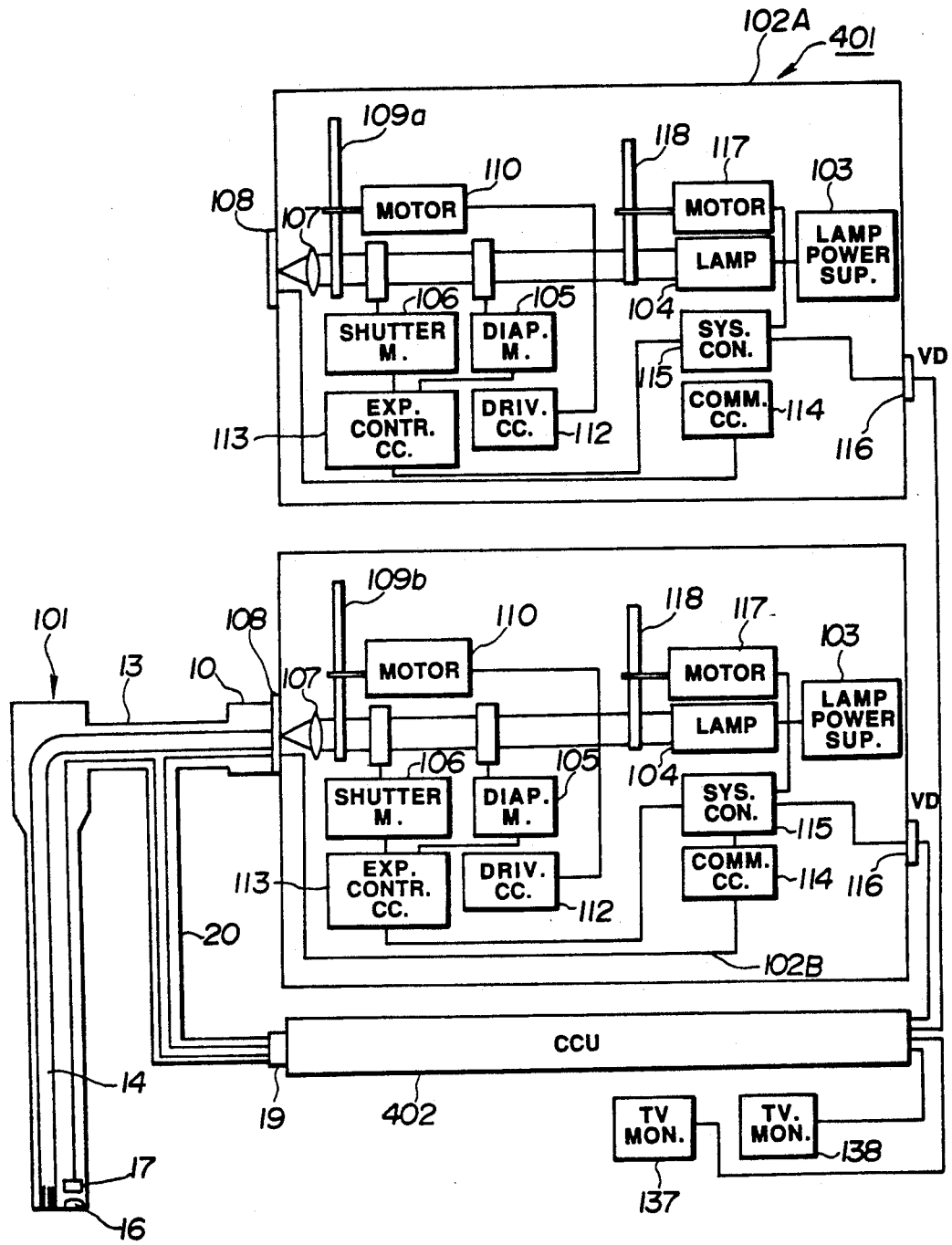
FIG. 22 is a formation diagram showing an endoscope apparatus of the fourth embodiment of the present invention.

FIG. 22 shows an endoscope apparatus apparatus 401 of the fourth embodiment in the present invention. This endoscope 401 consists of the electronic scope 101, the first light source 102A to which the electronic scope 101 can be connected, the second light source 102B, a CCU 402 and the TV monitors 137 and 138.

Figure 23A:
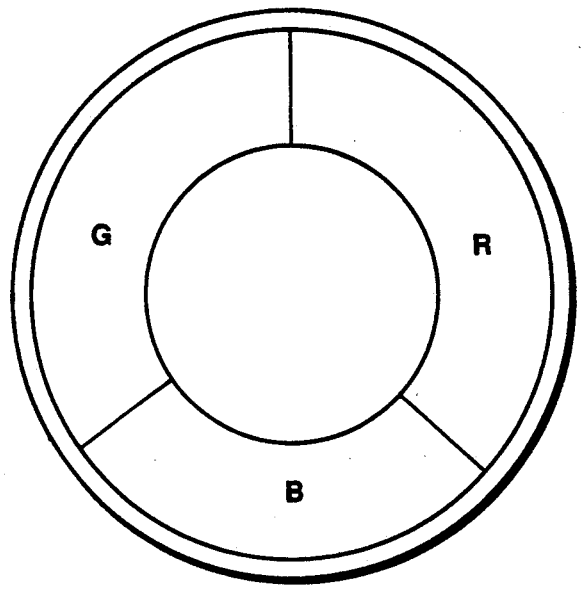
FIG. 23 is an explanatory view showing a rotary filter used in the fourth embodiment.
Figure 23B:
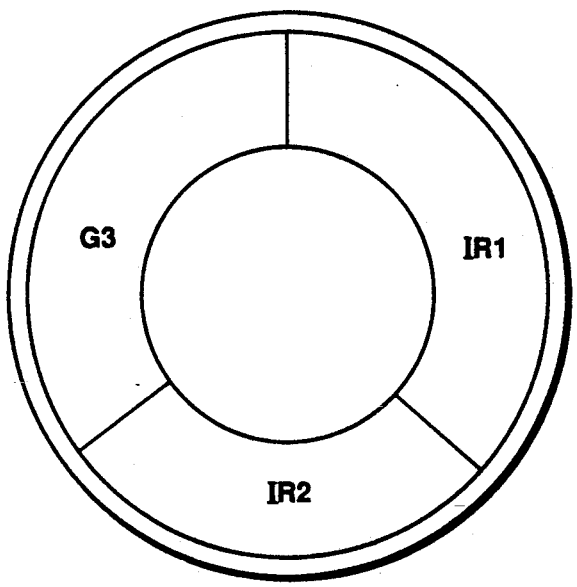

The first light source 102A and the second light source 102B do not contain a motor moving circuit 111 in the light source 102 shown in FIG. 18, and use rotary filters 109a and 109b shown in FIGS. 23a and 23b, respectively, instead of the rotary filter 109.

Also, the CCU 402 is provided with the signal processing system shown in FIG. 17. The CCU 402 transmits the synchronizing signal VD to the first light source 102A and the second light source 102B and makes the signal processing system and the illuminating system of the two light sources 102A and 102B be synchronized with each other, as explained in the first embodiment. The fourth embodiment also has the effect of the apparatus 100 explained in FIG. 17 with respect to the operational effect of the first embodiment.

Next, the modification of the embodiment of FIG. 17 will be explained.

Figure 24:
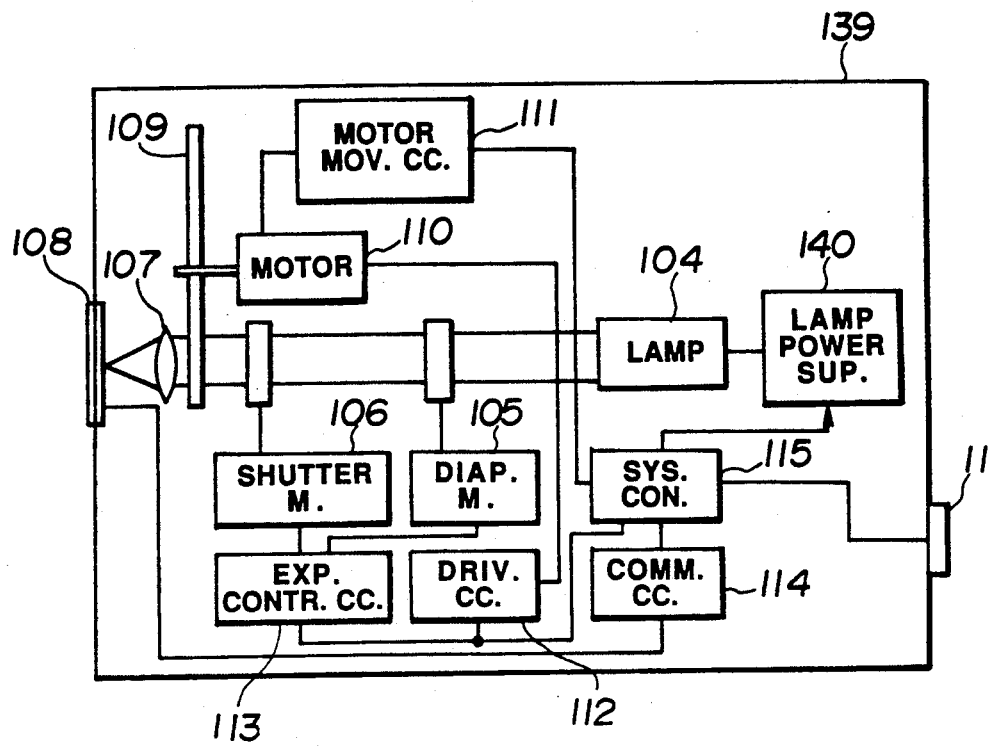
FIG. 24 is a formation diagram showing an endoscope apparatus having structure different from the structure in FIG. 17.
Figure 25A:
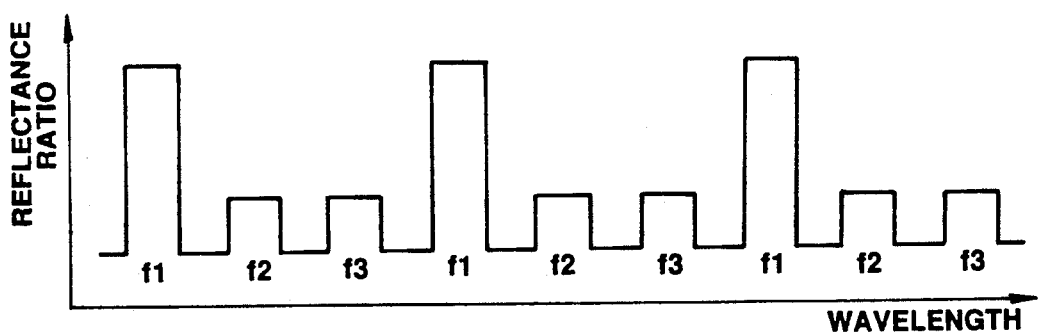
FIG. 25 is an explanatory view of an operation using a light source apparatus in FIG. 24.
Figure 25B:
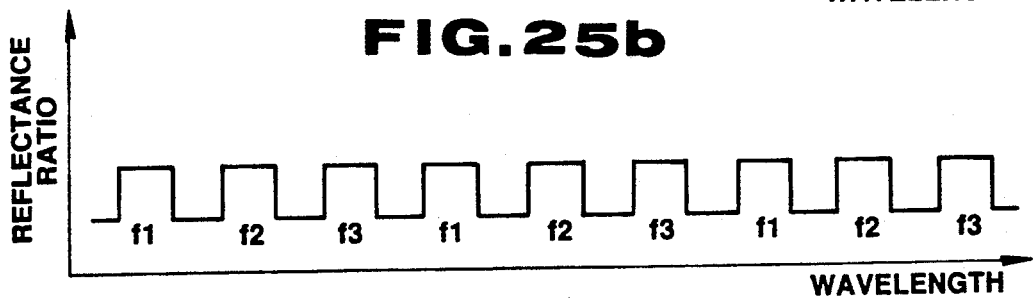

The endoscope apparatus in this modification uses a light source apparatus 139 as formed in FIG. 24 in the embodiment of FIG. 17. The light source apparatus 139 does not contain the motor 117 and the filter turret 118 in the light source apparatus 102 in FIG. 18, and also has the structure in which the driving current of a lamp power supply 103 is variable by the system controller 115 and used as a lamp power supply 140. Each color signal level obtained when a subject is imaged is detected in the WB adjusting circuit 122. Based on the information, the light source apparatus 139 controls the lamp power supply 140 in the apparatus 139, as shown in FIG. 25b, an approximately average level of each light color reflected from a subject, and an approximately uniform level of each color of reflected light by emitting the illuminating light strongly in the color signal of poor reflectance ratio shown in FIG. 25a.

The level difference of the obtained color signals is corrected and processed on the basis of the level difference of the illuminating light, as shown in the apparatus of FIG. 17, and displayed on the TV monitors 137 and 138.

By this modification, the same effect as the effect of the endoscope apparatus 101 shown in FIG. 17 is available without using various filters and also, an apparatus can be simplified. The rotary filter 109 in this modification is exchanged for the filters 109A and 109B shown in FIG. 23 so that a different embodiment can be formed.

Figure 26:
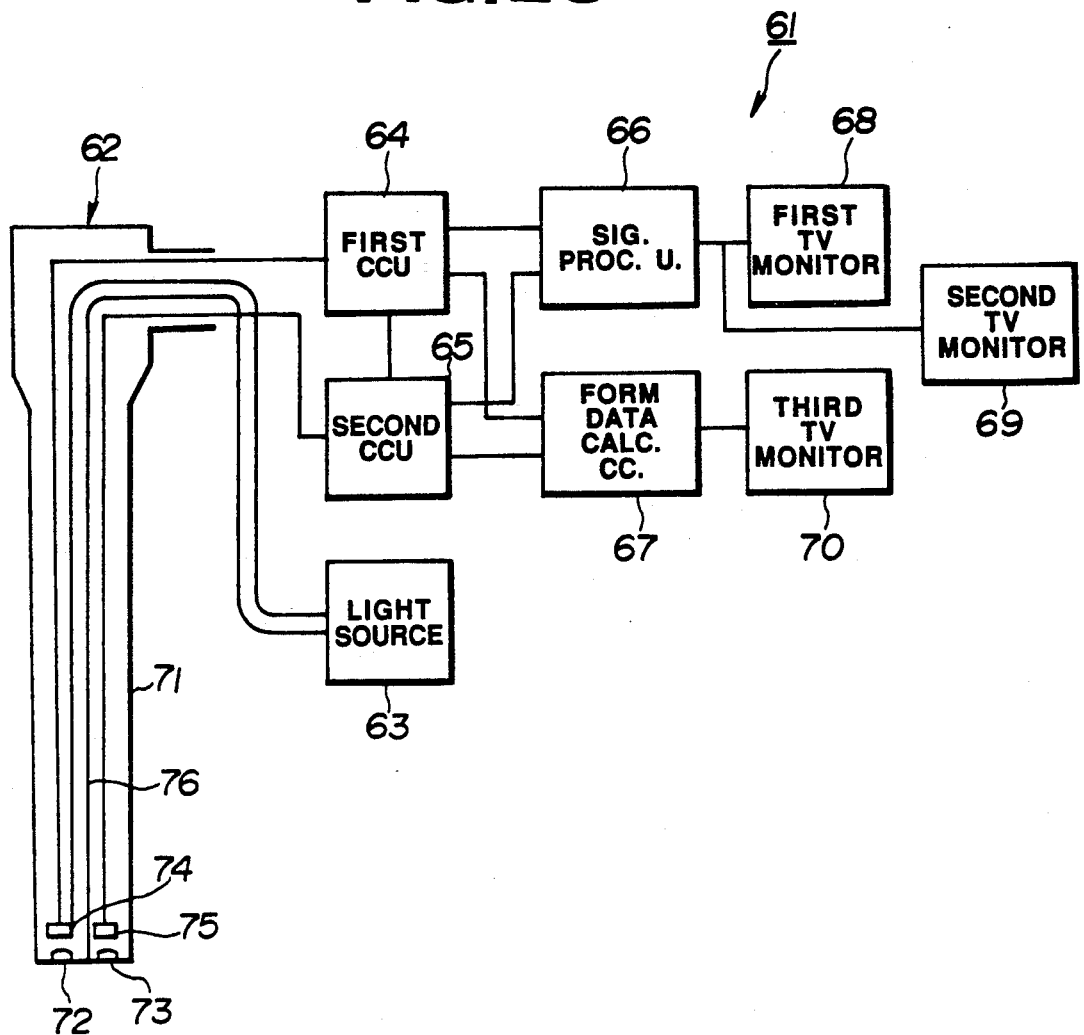
FIG. 26 is a formation diagram showing an endoscope apparatus for ordinary and special observation by synchronizing signal processing means of a plurality of apparatuses with one light source.

Next, an endoscope apparatus is shown in FIG. 26. In this apparatus, a plurality of signal processing units are synchronized with one light source and thus, an ordinary observation and special observation can be easily carried out.

The endoscope apparatus 61 includes a stereo electronic scope 62, a light source 63 supplying an illuminating light to the stereo electronic scope 62, a first CCU 64 and a second CCU 65 processing signals for the stereo electronic scope 62, a signal processing unit 66 processing the picture signal generated from the two CCUs 64 and 65, a form data calculating circuit 67 calculating a form data of a subject from the two picture signals, a first TV monitor 68 and a second TV monitor 69 indicating information by a signal processing unit 66 and a third TV monitor 70 displaying the form data calculated by the form data calculating circuit 67.

In the stereo electronic scope 62, objective lenses 72 and 73 are arranged separately in the distal end of an elongated insertable part 71. CCD 74 and 75 as imaging devices are arranged on the focal surface of each objective lens 72 and 73.

Figure 27:
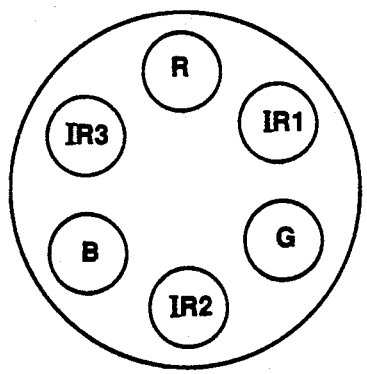
FIG. 27 is a front view showing a rotary filter used in a light source in FIG. 26.
Figure 28:
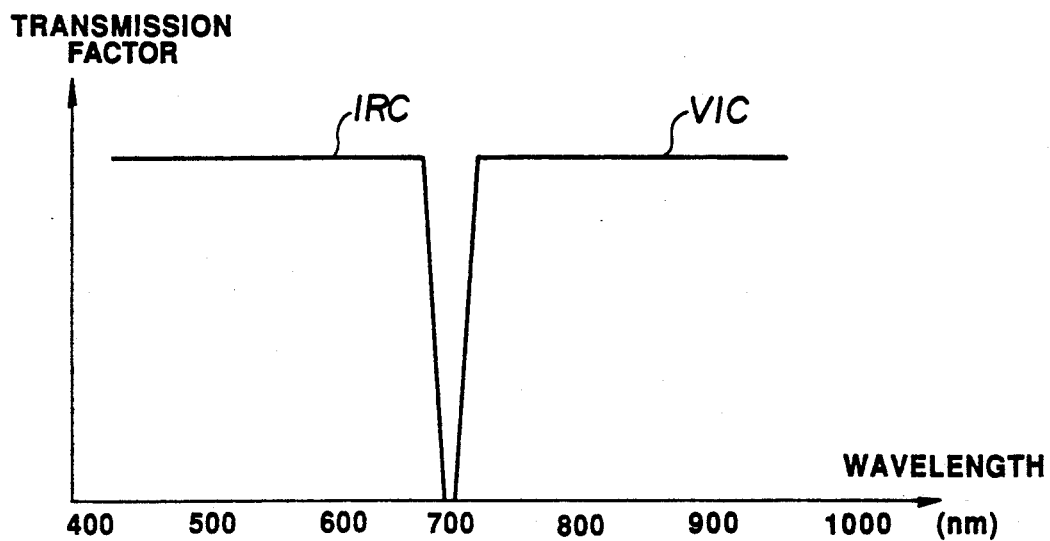
FIG. 28 is a characteristic diagram of a filter contained in a stereo electronic endoscope in FIG. 26.
Figure 29:
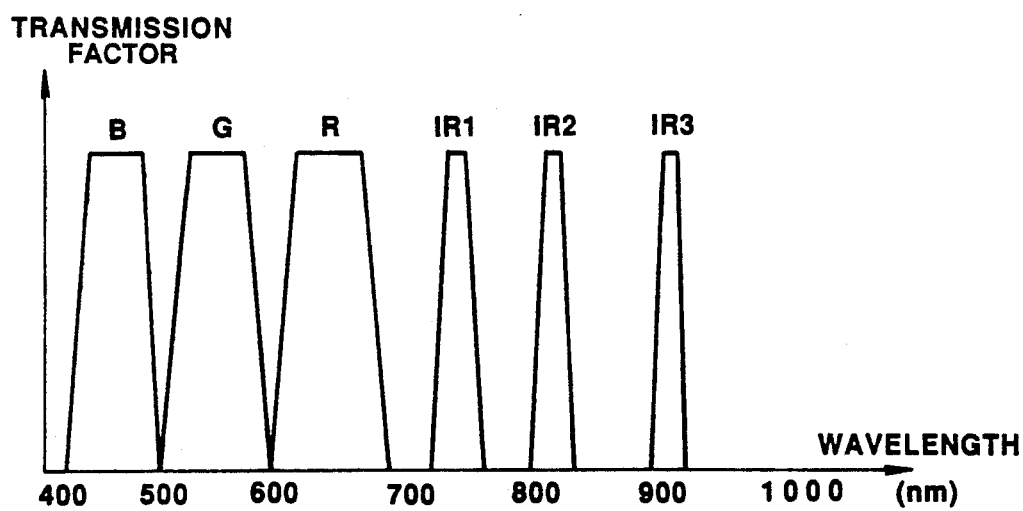
FIG. 29 is a characteristic diagram showing transmission factor characteristics of a filter fitted to a rotary filter in FIG. 27.

The CCD 74 and 75 have infrared cut characteristics IRC and visible cut characteristics VIC, respectively, as shown in FIG. 28. The side near the end surface of a light guide 76 is connected to the stereo electronic scope 62 through the insertable part 71 so that the light of each wavelength range of the spectral characteristics shown in FIG. 29 is supplied to the light guide 76 by the filter shown in FIG. 27 provided in a rotary filter for separating light which is stored in the light source 63. Thus, the light is emitted from the end surface of the tip side to the subject side.

The signal processing unit 66 measures the picture image of the living body functional information or displays for observing by processing the picture signal generated from the two CCUs 64 and 65. Thus, the structure of a visible picture image, that is, a normal picture image, is displayed or emphasized on the first TV monitor 68, and an infrared picture image is displayed on the second TV monitor 69.

Further, the form data calculating circuit 67 calculates a form data using the picture signal of a visible picture image and an infrared picture image, each of which has a parallax, and displays the calculated form data on the third TV monitor 70. Also, the light source 63 and the two CCD 64 and 65 transmit a synchronizing signal with each other through a signal line (not illustrated) and make the signal synchronize with each other.

The operation of the endoscope apparatus 61 will be explained as follows.

The rotary filter of the light source 63 is irradiated by spectral illuminating lights in the wavelength ranges in a time series as shown in FIG. 29. On the receiving light surface of the stereo electronic scope 62 provided with two receiving light sensitive ranges, two kinds of picture images in the infrared range and the visible range, respectively, are supplied from the two CCUs 64 and 65 by a timing (for example, when a picture image is supplied by an exposure period, the other is supplied by a transmitting period).

From the supplied picture signal, a form data of a subject is calculated in the form data calculating circuit 67 and displayed on the TV monitors 70 for displaying. Meanwhile, the visible picture image supplied to the signal processing unit 66 is fed to the TV monitor 68 as a normal picture image in the signal processing unit 66. Alternatively, an emphasis process, such as a form emphasis, or tone emphasis is applied to the visible picture and the picture is displayed on the TV monitor 68. Also, on the infrared picture image, various functional information of a living body is calculated by the calculation among picture images of each wavelength and the result of the calculation is displayed on the TV monitor 69.

By this endoscope apparatus 61, a form data of a subject is calculated in the same way as an ordinary stereoscope. At the same time, both an ordinary visible picture image and functional information of a living body are simultaneously displayed or measured so that a functional picture image of a living body, such as a form data of a living body, an ordinary observation picture image and blood flow, and the degree of saturation with oxygen in hemoglobin, can be simultaneously measured; thus the diagnostic ability thereof is improved.

Figure 30:
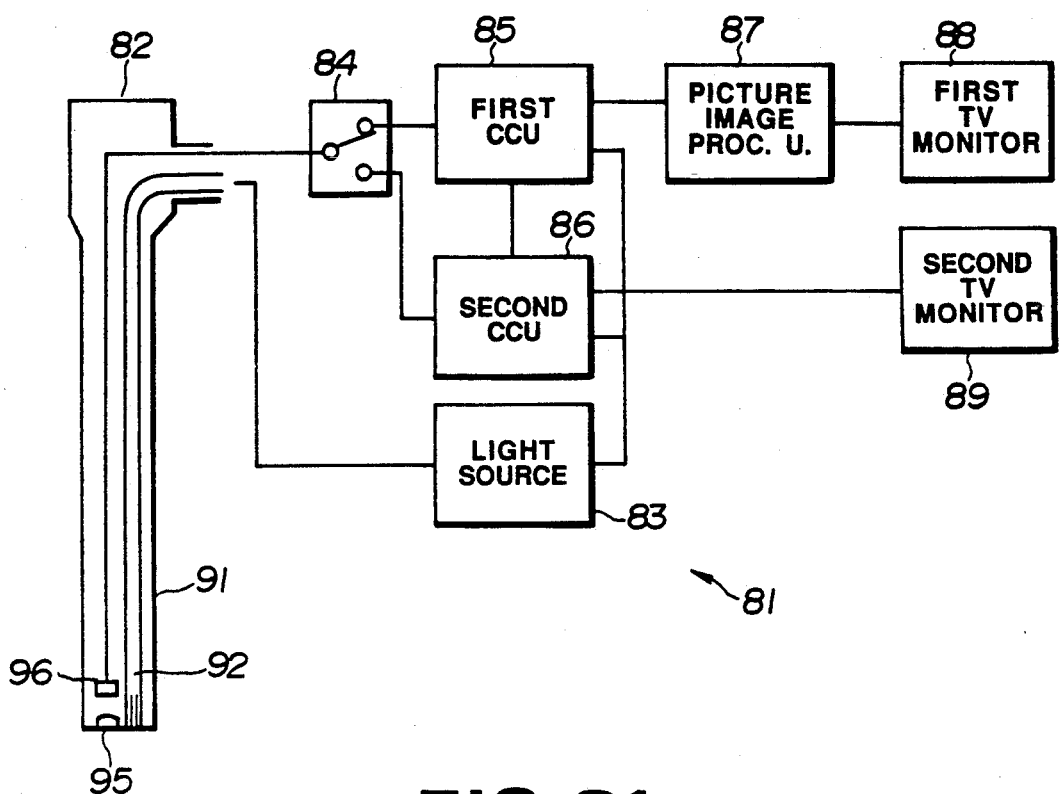
FIG. 30 is a formation diagram showing an endoscope apparatus having structure different from the structure in FIG. 26.

FIG. 30 shows an endoscope apparatus 81 which generates a λ-corrected picture signal from an ordinary observation and a picture signal without λ-correction for a special observation, and measures or displays an image after processed by a calculating apparatus among picture images.

The endoscope apparatus 81 includes of an electronic scope 82 which can image even an infrared rays range, a light source 83 supplying an illuminating light to the electronic scope 82, a first CCU 85 and second CCU 86 selectively connected to the electronic scope 82 through a switching apparatus 84 connected to the electronic scope 82, a picture image processing unit 87 imaging living body functional information by calculating among picture images for the output signal of the first CCU 85 and a first and second TV monitors 88 and 89 on which the output signals from the picture image processing unit 87 and the second CCU 86 are displayed, respectively.

In the electronic scope 82, a light guide 92 is inserted into an elongated insertable part 91 and an illuminating light is supplied from the light source 83 by connecting the light guide 92 to the light source 83.

Figure 31:
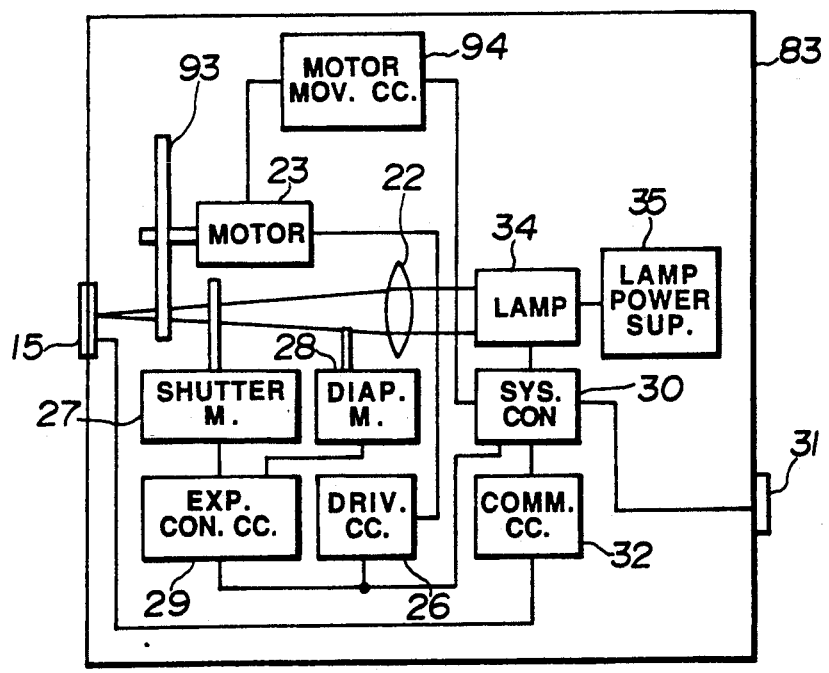
FIG. 31 is a formation diagram showing a light source in FIG. 30.

The structure of the light source 83 is shown in FIG. 31. In the light source 83, a rotary filter 93 provided with the filters shown in FIG. 32 is used instead of the rotary filter 36 in the second light spruce 4 shown in FIG. 1, and also contains a motor moving circuit 94 moving the rotary filter 93 with a motor 23 in the perpendicular direction to the optical axis.

Figure 32:
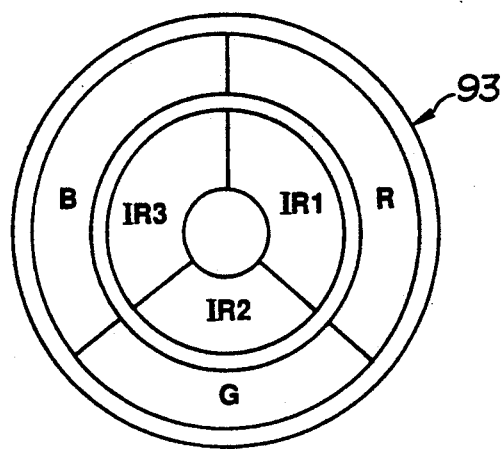
FIG. 32 is a front view showing a rotary filter contained in a light source in FIG. 31.

The rotary filter 93 is provided with filters R, G and B in its outer circumference, as shown in FIG. 32, and filters IR1, IR2 and IR3 on the inside portions therefore. The rotary filter 93 moves with the motor 23 in the perpendicular direction to the optical axis by the motor moving circuit 94 so that a combination of filters for separating colors of an illuminating light can be switched.

To the distal end of the elongated insertable part 91, an objective lens 95 and a CCD 96 which is placed on the focal surface of the lens 95 are fitted. The CCD 96 has a characteristic of the sensitivity in an infrared range without using an infrared cut filter. The output signal of the CCD 96 goes into the first CCD 85 and second CCD 86 through the switching apparatus 84.

The first CCU 85 processes signals (λ-correction is not performed) for the picture signal imaged by the illuminating light through the filters IR1, IR2 and IR3. The output signal of the CCU 85 is fed to the picture image processing unit 87.

Also, the second CCU 86 processes signals (λ-correction is performed) for the picture signals imaged by the illuminating light through the filters R, G and B and displays them on the TV monitor 89.

The first and second CCU 85 and 86 are connected to the light source 83 and the two CCUs 85 and 86 are synchronized with each other to be operated.

The operation of the endoscope apparatus 81 will be explained as follows. The light source 83 lights a lamp 34 by a lamp power supply 35. The lamp 34 emits lights from a visible light range to an infrared rays range and supplies the lights for illumination to an electronic scope 82 through an output connector 15 which is a connector to the scope 82 after converged by a lens 22 for converging light to an electronic scope 82.

The illuminating light emitted from the lamp 34 is variably changed to the suitable quantity of light by diaphragm means 28 so as to apply a suitable exposure to a subject by the control of an exposure controlling circuit 29. When the electronic scope 82 is removed from the output connector 15, shutter means 27 which cuts the suitable quantity of light is controlled by the exposure controlling circuit 29, as well. The illuminating light is controlled to the suitable quantity of light by the diaphragm means 28. The rotary filter 93 is rotated by the motor 23 in which its rotation number is controlled by a driving circuit 26. The rotary filter 93 is formed as shown in FIG. 32 in order to separate colors by different combinations of filters in time series. Thus, the outer filters R, G and B separate colors for an ordinary observation and the inner filters IR1, IR2 and IR3 separate colors for detecting the quantity of pigments in a living body and observing functional information of a living body. The combinations of the two kinds of inside and outside filters can be changed for separating colors of an illuminating light converged by the lens 22, because the position of the rotary filter 93 moves with the movement of the motor 23 by the motor moving circuit 94.

When an ordinary observation is performed at the electronic scope 82, the signal for discriminating a video signal level and CCU is supplied from the output connector 15 to the light source 83 through an electronic scope 82 and the CCU 86 if the CCU 86 is selected by the switching apparatus 84. The signal supplied to the light source 83 goes into a system controller 30 by a communication circuit 32 and the filters R, G and B for an ordinary observation of the rotary filter 93 are selected by the motor moving circuit 94.

Meanwhile, when the CCU 85 is selected by the switching apparatus 84, the filters IR1, IR2 and IR3 for a functional picture image observation are selected just like the above mentioned by the motor moving circuit 94 by using the signal from the CCU 85. Since the CCUs 85 and 86 are synchronized with each other through the light source 83, a picture image does not fall into disorder even if the picture image is switched by the switching apparatus 84. The picture signal generated from the CCU 85 is processed to calculate the functional information of a living body by the calculation among picture images in the picture image processing unit 87 and by the observation of the pigment distribution in a living body, so that the processed signal is displayed as a picture image on the TV monitor 88.

In this endoscope apparatus 81, as mentioned above, even when the CCU for ordinary observation and living body functional picture image observation and a plurality of CCU 85 and 86 are used, the CCU can be used without making a picture image fall into disorder, so that an ordinary observation, infrared picture image observation and a living body functional picture image observation (blood flow, degree of saturation with oxygen) can be easily carried out, and the functional information of a living body can be easily and effectively observed and measured.

Next, an endoscope apparatus 201 in which the operability of switching between an ordinary observation and a blood flow observation is improved will be explained by referring to FIG. 33.

The endoscope apparatus 201 contains imaging means and consists of an infrared rays electronic scope 202 having sensitivity in infrared rays, a first light source 204 supplying a first illuminating light and containing scope detecting signal generating circuit which generates a scope detecting signal when a connector 214 of the infrared rays electronic scope 202 is connected to an output connector 203a, a second light source 205 supplying a second illuminating light to the infrared rays electronic scope 202 when the connector 214 is connected to the output connector 203b, a CCU 206 processing signals for the infrared rays electronic scope 202, a TV monitor 207 displaying a video signal processed in the CCU 206 and a switching unit 208 switching from the light source connected with the infrared rays electronic scope 202 to the CCU 206 and vice versa based on the scope detecting signal generated from the first light source 204.

When the scope detecting signal is not generated, that is, when the infrared rays electronic scope 202 is connected with the second light source 205, the light source for an ordinary observation, that is, the second light source 205 and the CCU 206 are connected to the infrared rays electronic scope 202 in an operating condition. Therefore, when the scope detecting signal is generated, in other words, the infrared rays electronic scope 202 is connected to the first light source 204, the first light source 204 and the CCU 206 are automatically switched to an operating condition of the infrared rays electronic scope 202.

The infrared rays electronic scope 202 has an elongated insertable part 211 and a broad operating part 212 formed at the rear end of the insertable part 211, an universal cable 213 extended from the operating part 212. Thus, a connector 214 at the end of the cable 213 can be connected to the output connector 203a of the first light source 204 or the output connector 203b of the second light source 205. A cable 215 is further extended from the connector 214 and a connector 216 at the end of the cable 215 can be connected to the CCU 206.

Also, a light guide (not illustrated) for transmitting an illuminating light is inserted into the insertable part 211. The light guide is also inserted into the universal cable 213. The connector 214 is connected to the output connector 203a of the first light source 204 or the output connector 203b of the second light source 205 so that an illuminating light is supplied from the first light source 204 or second light source 205 to the incident end surface of the light guide.

In the above mentioned infrared rays electronic scope 202, an infrared cut filter fitted to the electronic scope for an ordinary observation is removed and the coating of the lens fitted to the tip of the CCD is exchanged for a coating which can be used for an infrared observation so that the scope 202 has sensitivity in an infrared range with an ordinary visible range.

The first light source 204 is formed of a rotary filter 218 which transmits the wavelength range of, for example, a blood flow observation and which is different from the rotary filter 217 for an ordinary observation, such as, color filters R, G and B of the second light source 205. Thus, the first light source 204 can supply an illuminating light which is different from the illuminating light for an ordinary observation by the second light source 205 to the light guide of the infrared rays electronic scope 202.

Figure 34:
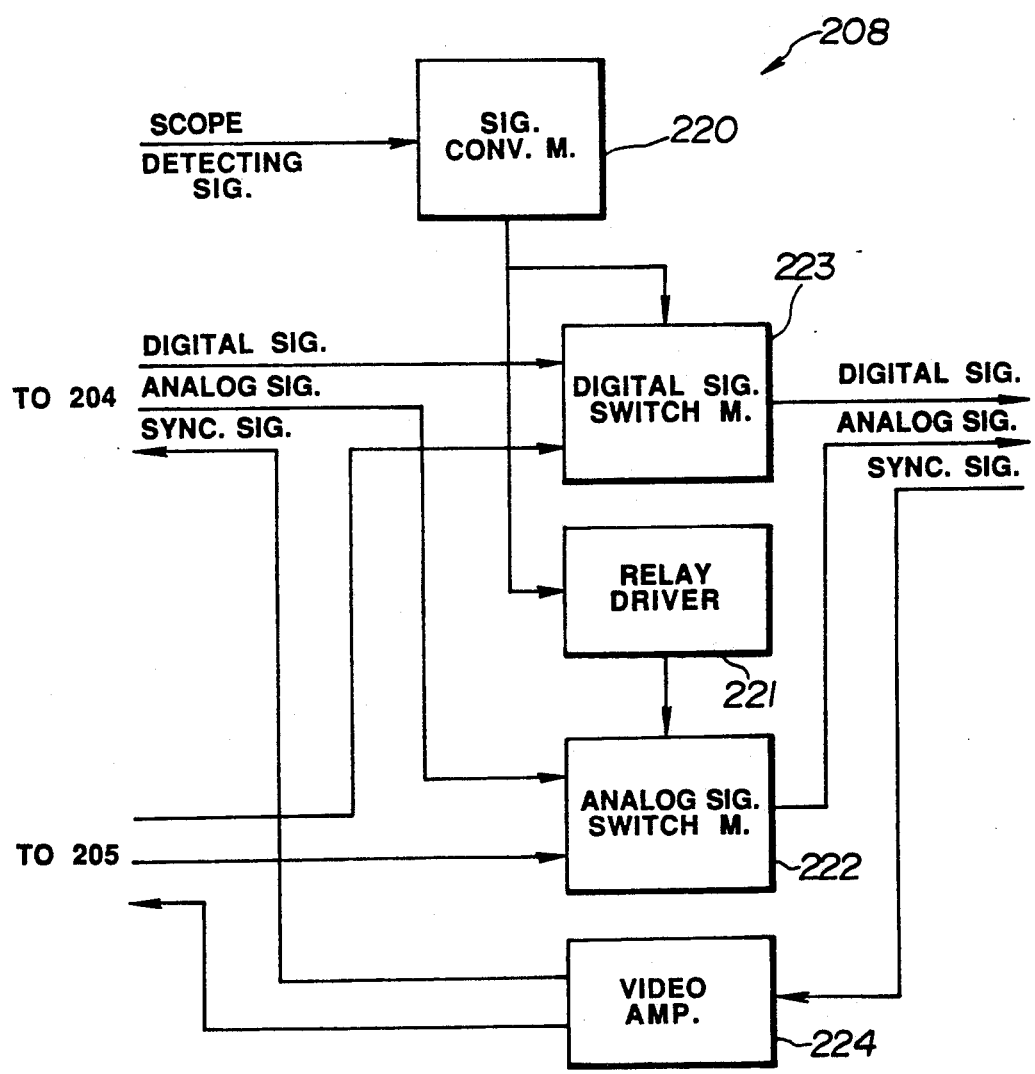
FIG. 34 is a block diagram of a switching unit formation.

As shown in FIG. 34, the switching unit 208 has signal converting means 220 converting a scope detecting signal which is generated when the infrared rays electronic scope 202 is connected to the output connector 203a of the first light source 204 into a control signal, analog signal switching means 222 for switching an analog signal of the signal which adjusts light intensity through a relay driver 221 based on the converted control signal, from the second light source 205 to the first light source 204, digital signal for switching means 223 switching a digital signal of the signal, such as the signal designating the R signal to write the signals R, G and B in a memory correctly, from the second light source 205 to the first light source 204 and a video amplifier 224 for generating a composite sink signal to the light sources 204 and 205 to synchronize the two light sources 204 and 205 with the CCU 206 at all times.

Like the light sources 3A and 3B shown in FIG. 1, the first light source 204 and second light source 205 shown in FIG. 33 have signal processing systems 231a and 231b (shown by dotted lines), such as the system controller 30 or the communication circuit 32. The signal processing system 231a is also provided with a scope detecting signal generating circuit. Further, the CCU 206 has a signal processing system 232 which generates three primary color signals R, G and B from the signal which is imaged under the frame sequential illumination by the second light source 205, and a frame memory 233 which stores the signals R, G and B. Further, the signal processing system 231a of the CCU 206 also contains a signal processing function for the signal imaged under the illumination by the first light source 204. The signal process for the two kinds of signals is controlled by the signal of the switching unit 208.

The operation of the endoscope apparatus 201 formed as mentioned above is explained as follows. When the ordinary observation is performed, the infrared rays electronic scope 202 is connected to the second light source 205. The switching unit 208 always supplies the signals for synchronizing the rotary filter with the signal process of the CCU 206 to the two light sources 204 and 205. When the infrared rays electronic scope 202 is not connected to the first light source 204, a signal which designates the R signal for writing the signals R, G and B in a memory correctly is supplied from the CCU 206 to the light source 205 for an ordinary observation. Thus, color picture images R, G and B for an ordinary observation are displayed on the TV monitor 207.

In the meantime, the infrared rays electronic scope 202 is connected to the output connector 203a of the first light source 204 so that a scope detecting signal is generated from the first light source 204 to the switching unit 208. Then, the switching unit 208 generates a control signal for switching signals based on the scope detecting signal, and the connection of each signal is switched from the second light source 205 to the first light source 204 so that a picture image obtained by the illuminating light of the first light source 204 can be displayed on the TV monitor 207.

Also, the first light source 204 does not generate a scope detecting signal by the removal of the infrared rays electronic scope 202 from the output connector 203a of the first light source 204. Since the switching unit 208 always connects the light sources for an ordinary observation (i.e., the second light source 205 and the CCU 206) when the infrared rays electronic scope 202 is not connected to the switching unit 208, the connection of the first light source 204 is switched to the second light source 205.

With the apparatus 201, an observation picture image to be observed can be easily and immediately displayed on the TV monitor 207 by switching the infrared rays electronic scope 202 from the second light source 205 to the first light source 204. Also, although it has been difficult to diagnose a pathologically changed part by an ordinary observation, the part can be easily diagnosed based on the picture image by the first light source 204, so that it is also effective to improve the diagnosing ability. Further, the picture image does not fall into disorder when switched, because the two light sources 204 and 205 are always synchronized with the CCU 206 as in the first embodiment.

Figure 35:
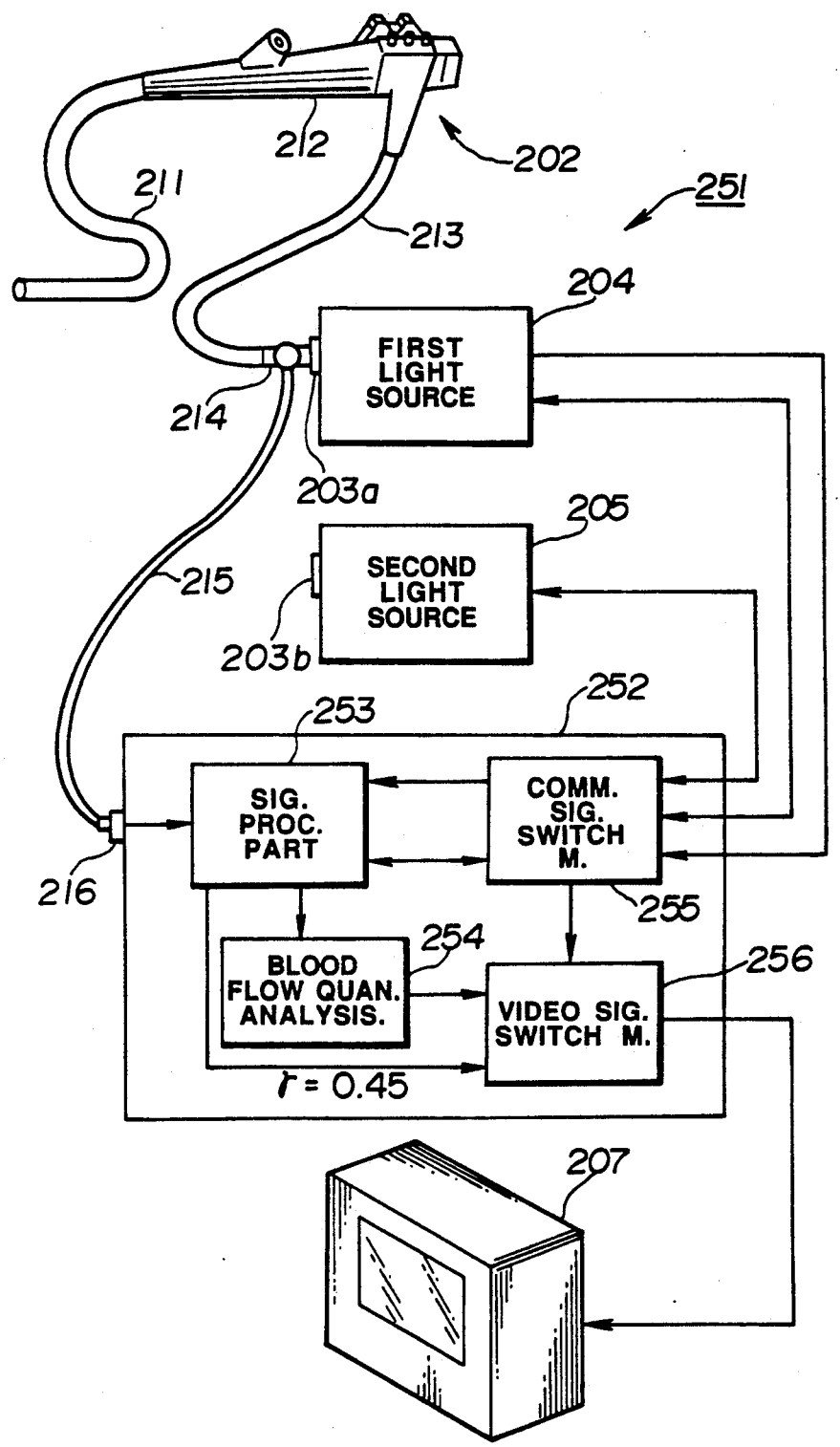
FIG. 35 is a formation diagram showing a modification of an endoscope apparatus in FIG. 33.

FIG. 35 shows an endoscope apparatus 251 of the modification of FIG. 33. In this endoscope apparatus 251, the infrared rays electronic scope 202, the first light source 204, the second light source 205 and the TV monitor 207 are shown in the same way as the endoscope apparatus 201 in FIG. 33. A CCU 252 in this apparatus 251 includes a signal processing part 253 for processing the video signal transmitted from the infrared rays electronic scope 202, blood flow analysis means 254 for calculating the quantity of blood flow based on the transmitted video signal, communication signal switching means 255 for switching a signal to the light source selected from the two light sources and video signal switching means 256 for replacing the processed video signal with the picture image in which a blood flow is analyzed.

Next, the operation of the apparatus 251 will be explained. When an ordinary observation is carried out, the infrared rays electronic scope 202 is connected to the second light source 205. Since a scope detecting signal is not transmitted to the communication signal switching means 255 when the infrared rays electronic scope 202 is connected to the second light source 205, the information from the second light source 205 is transmitted to the signal processing part 253 (through the communication signal switching means 255) and, at the same time, an ordinary observation picture image selecting signal is transmitted to the video signal switching means 256. The signal processing part 253 transmits an ordinary observation picture signal to the video signal switching means 256. In the video signal switching means 256, an ordinary observation picture image selecting signal transmitted from the communication signal switching means 255 is selected and the ordinary observation picture image is displayed on the TV monitor 207.

Meanwhile, by the connection of the infrared rays electronic scope 202 and the first light source 204, the communication signal switching means 255 makes the first light source 204 and the CCU 206 a connecting condition by using the scope detecting signal generated from the first light source 204. When the scope detecting signal is transmitted from the first light source 204 to the communication signal switching means 255, the information from the first light source 204 is transmitted to the signal processing part 253 and the blood flow picture image selecting signal is transmitted to the video signal switching means 256.

When the signal processing part 253 receives the signal from the first light source 204, the $\gamma$-correction of the video signal from the infrared rays electronic scope 202 is removed (that is, $\gamma=1$), and the video signal is transmitted to a blood flow analysis means 254. When the blood flow analysis means 254 receives the video signal from the signal processing part 253, the calculation between two picture images imaged in two narrow bands of wavelengths, respectively, is carried out and the quantity of blood flow is determined. Then, the result of the calculation of the blood flow picture signal and blood flow quantity is transmitted to the video signal switching means 256. The video signal switching means selects the result of the calculation based on the blood flow picture signal transmitted from the communication signal switching means 255 and the result of the calculation is displayed on the TV monitor 207.

In this apparatus 251, when the infrared rays electronic scope 202 is connected to a light source to be desired, the $\gamma$-correction is immediately removed and the quantity of blood flow can be very precisely obtained. Also, the diagnostic ability is improved because the quantity of blood flow is displayed in a quantitative manner. Further, an ordinary observation picture image and blood flow observation picture image can be displayed at the same time on the TV monitor 207 by making, for example, a freeze picture image of the ordinary observation picture image.

Also, different embodiments can be formed by the combinations of the parts of the above mentioned each embodiment. These embodiments also belong to the present invention.

While the invention has been particularly shown and described in reference to preferred embodiments thereof, it will be understood by those skilled in the art that changes in form and details may be made therein without departing from the spirit and scope of the invention.

What is claimed is:

1. An endoscope system comprising:
    an electronic type endoscope having an elongated insertable part, a light guide inserted into the insertable part transmitting an illuminating light supplied to an end surface of the light guide and emitting from the other end surface, an objective optical system provided on a tip side of said insertable part and a solid state imaging device photoelectrically converting an optical image based on the objective optical system;
    a first light source apparatus frame sequentially supplying a plurality of illuminating lights in different wavelength ranges to the end surface of said light guide by connecting said electronic type endoscope to the first light source apparatus;
    a second light source apparatus supplying illuminating lights in different wavelength ranges from the ranges of said illuminating lights emitted from said first light source apparatus by connecting said electronic type endoscope to the second light source apparatus;
    synchronizing control means generating a synchronizing signal synchronizing at least an illuminating period of the plurality of illuminating lights emitted from said first light source apparatus with at least an illuminating period of the illuminating lights emitted from said second light source apparatus;
    a driving circuit applying a driving signal to said solid state imaging device at a period synchronized with said synchronizing signal and outputting a picture signal photoelectrically converted;
    a video signal processing circuit processing said picture signal at a period synchronized with said synchronizing signal and producing a video signal; and
    a monitor means for displaying said video signal.

2. The system according to claim 1, wherein said electronic type endoscope is an electronic scope provided with a photoelectrically converted surface of said solid state imaging device being arranged on the focal surface of said objective optical system.

3. The system according to claim 1, wherein said synchronizing control means is provided in a camera control unit housing said driving circuit and said video signal processing circuit.

4. The system according to claim 1, wherein said driving circuit synchronizes said driving signal with each shading period of said first light source apparatus without emitting said illuminating lights based on said synchronizing signal and emits said driving signal.

5. The system according to claim 1, wherein said driving circuit synchronizes said driving signal with each shading period of said second light source apparatus without emitting said illuminating lights based on said synchronizing signal and emits said driving signal.

6. The system according to claim 1, wherein said second light source apparatus has a laser beam source emitting a laser beam of a single narrow wavelength range and said laser beam is supplied to said light guide through a plurality of apertures provided on a disk rotatively driven.

7. The system according to claim 1, wherein said video signal processing circuit processes common signals when said light guide is connected to one of the light source apparatuses.

8. The system according to claim 1, wherein the quantity of illuminating light supplied from said first light source apparatus and said second light source apparatus to said light guide is controlled corresponding to a control signal supplied from said video signal processing circuit.

9. The system according to claim 1, wherein said first light source apparatus rotatively drives a rotary filter fitting a plurality of filters having different transmitting wavelength ranges in a circumference direction for a light emitted from a lamp by using a motor and emits said illuminating lights frame sequentially through said filter arranged in a position facing said lamp.

10. The system according to claim 9, wherein said plurality of filters transmit wavelength ranges in a visible range, respectively.

11. The system according to claim 9, wherein said first light source apparatus has detecting means for detecting a start/end of an emitting period emitting said illuminating lights and a PLL circuit for synchronizing output of the detecting means with said synchronizing signal of said synchronizing control means and controls a rotation of said motor by the output of said PLL circuit.

12. The system according to claim 1, wherein said second light source rotatively drives a rotary filter fitting a plurality of a filters having different transmitting wavelength ranges in a circumference direction for a light emitted from a lamp by using a motor and emits said illuminating lights frame sequentially through said filter arranged in a position facing said lamp.

13. The system according to claim 12, wherein said plurality of filters have narrow range filters transmitting wavelengths of a narrow range in an infrared range.

14. The system according to claim 12, wherein said second light source apparatus has detecting means for detecting a start/end of an emitting period emitting said illuminating lights and a PLL circuit for synchronizing output of the detecting means with said synchronizing signal of said synchronizing control means and controls a rotation of said motor by the output of said PLL circuit.

15. The system according to claim 1, wherein said first light source apparatus has quantity of light changing means changing quantity of illuminating light supplied to said light guide.

16. The system according to claim 15, wherein said quantity of light changing means can selectively and variably adjust quantity of light characteristics by a plurality of illuminating lights supplied to said light guide.

17. The system according to claim 16, wherein said quantity of light changing means can selectively and variably adjust said quantity of light characteristics so that levels of picture signal imaged by said solid state imaging device under illuminating lights, respectively, are equal.

18. The system according to claim 1, wherein said second light source apparatus has quantity of light changing means changing quantity of illuminating light supplied to said light guide.

19. The system according to claim 18, wherein said second light source can selectively and variably adjust quantity of light characteristics for the plurality of illuminating lights when illuminating lights supplied to said light guide have a plurality of wavelength ranges.

20. The system according to claim 19, wherein said quantity of light changing means can selectively and variably adjust said quantity of light characteristics so that levels of picture signal imaged by said solid state imaging device under illuminating lights, respectively, are equal.

21. The system according to claim 1, wherein said video signal processing circuit has a first video signal processing function corresponding to a case of said light guide connected to said first light source apparatus and a second video signal processing function corresponding to a case of said light guide connected to said second light source apparatus.

22. The system according to claim 21, wherein said first video signal processing function is different from said second video processing function.

23. The system according to claim 22, wherein said first video signal processing function and said second video signal processing function can be selected.

24. The system according to claim 22, wherein said first video signal processing function and said second video signal processing function are selected corresponding to the light source apparatus connected with said light guide.

* * * * *